(12) United States Patent
Zheng et al.

(10) Patent No.: US 7,226,779 B2
(45) Date of Patent: Jun. 5, 2007

(54) HYBRID ADENOVIRAL VECTOR

(75) Inventors: Changyu Zheng, Rockville, MD (US);
Bruce J. Baum, Bethesda, MD (US);
Brian C. O'Connell, Dublin (IE)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 33 days.

(21) Appl. No.: 10/470,784

(22) PCT Filed: Jan. 25, 2002

(86) PCT No.: PCT/US02/02279

§ 371 (c)(1),
(2), (4) Date: Jul. 29, 2003

(87) PCT Pub. No.: WO02/061104

PCT Pub. Date: Aug. 8, 2002

(65) Prior Publication Data

US 2004/0248827 A1    Dec. 9, 2004

Related U.S. Application Data

(60) Provisional application No. 60/265,198, filed on Jan. 30, 2001.

(51) Int. Cl.
*C12N 15/00* (2006.01)
(52) U.S. Cl. .................................. 435/320.1
(58) Field of Classification Search ............. 435/320.1; 432/320.1
See application file for complete search history.

(56) References Cited

U.S. PATENT DOCUMENTS

| | | | |
|---|---|---|---|
| 5,585,362 A | | 12/1996 | Wilson et al. |
| 5,681,746 A | * | 10/1997 | Bodner et al. ............... 435/350 |
| 5,948,675 A | | 9/1999 | Klatzmann et al. |
| 6,001,557 A | | 12/1999 | Wilson et al. |
| 6,303,380 B1 | | 10/2001 | Lin et al. |
| 6,410,011 B1 | * | 6/2002 | Branellec et al. ........... 424/93.2 |
| 2002/0150876 A1 | * | 10/2002 | Pippig et al. ................. 435/4 |
| 2004/0115788 A1 | | 6/2004 | Zheng et al. |
| 2004/0248827 A1 | | 12/2004 | Zheng et al. |

FOREIGN PATENT DOCUMENTS

| | | |
|---|---|---|
| WO | WO 96/05321 | 2/1996 |
| WO | WO 97/25446 | 9/1997 |
| WO | WO 98/22143 | 5/1998 |
| WO | WO 99/32647 | 7/1999 |
| WO | WO 00/56910 | 9/2000 |
| WO | WO 01/55362 | 8/2001 |
| WO | WO 02/061104 | 8/2002 |

OTHER PUBLICATIONS

U.S. Appl. No. 60/179,327.*
Babincova et al. Life and Medical Sciences Online (2000), pp. 1-4.*
U.S. Appl. No. 60/266,331.*
Barry et al. Human Gene Therapy, 12:131-139, 2001.*
Basak et al., "Modifying Adenoviral Vectors for Use as Gene-Based Cancer Vaccines," *Viral Immunol.* 17(2):182-196, 2004.
Dang et al., "Gene Therapy and Translational Cancer Research," *Clin. Cancer Res.* 5:471-474, 1999.
Ratner et al., "Complete nucleotide sequence of the AIDS virus, HTLV-III," *Nature* 313:277-284, 1985.
Bilbao et al., *The FASEB Journal* 11:624-635, 1997.
Caplen et al., *Gene Therapy* 6:454-459, 1999.
Duisit et al., *Human Gene Therapy* 10:189-200, 1999.
Feng et al., *Nature Biotechnology* 15:866-870, 1997.
Lin et al.,, *Gene Therapy* 5:1251-1258, 1998.
Link, *Nature Biotechnology* 18:150-151, 2000.
Robbins et al., *Pharmacol. Ther.* 80(1):35-47, 1998.
Sivak et al., *Molecular and Cellular Biology* 19(1):155-163, 1999.
Stone et al., *Journal of Endocrinology* 164:103-118, 2000.
Vanderwaak et al., *Gynecologic Oncology* 74:227-234, 1999.
Zheng et al., *Nature Biotechnology* 18:176-180, 2000.

* cited by examiner

*Primary Examiner*—Brian Whiteman
(74) *Attorney, Agent, or Firm*—Klarquist Sparkman, LLP

(57) ABSTRACT

An adenoviral vector is disclosed that includes two adenoviral ITRs, wherein the two adenoviral ITRs flank a packaging signal and a single retroviral LTR operably linked to a nucleic acid sequence of interest, wherein the adenoviral vector does not include a nucleic acid sequence encoding the retroviral structural proteins and wherein the adenoviral vector does not include a second retroviral LTR. In one embodiment, a method for transforming a cell is disclosed. In another embodiment, a method is disclosed for introducing a transgene into a cell with a single viral vector. In a further embodiment, a method is provided for preventing or treating disorder in a subject. A pharmaceutical composition is also provided.

29 Claims, 16 Drawing Sheets

A. Ad5'LTR-luc

B. AdCMV-luc

A. PCR design to detect integrase and reverse transcriptasegenes

B. Integrase

C. Reverse transcriptase

D. Integrase

E. Reverse transcriptase

A. Dividing Cells

B. Non-Dividing Cells

C. A5 Cloned Cell

D. Rat Submandibular Gland

A. Diagram of PCR design to detect integration

B. PCR control assay

C. Tested samples

A. Diagram of *Bam* HI and *Nco* I sites in Ad5′LTR-luc and probes used for Southern hybridization

B.

A. Diagram of *Spe* I site in Ad5'LTR-luc and probes used for Southern hybridization

B.

A. Diagram of *Bam* HI sites in Ad5'LTR-luc and probes used for Southern hybridization

B.

A. Diagram of *Bam* HI sites in AdCMV-luc and probes used for Southern hybridization

B.

A. Diagram of *Xho* I sites in Ad5'LTR-luc and probes used for Southern hybridization

B.

A. Diagram of *Kpn* I sites in Ad5'LTR-luc and probes used for Southern hybridization

B.

A. Diagram of *Nco* I sites in AdCMV-luc and probes used for Southern hybridization

B.

HYBRID ADENOVIRAL VECTOR

PRIORITY CLAIM

This is a § 371 U.S. national stage of PCT/US02/02279, filed Jan. 25, 2002, which was published in English under PCT Article 21(2), and claims the benefit of U.S. Provisional Application No. 60/265,198, filed Jan. 30, 2001.

FIELD OF THE INVENTION

This invention relates to the field of viral vectors and the transduction of cells, more specifically to hybrid adenoviral vectors and their use in the transduction of cells in vitro or in vivo.

BACKGROUND

The transfer of genes into cells provides a means to determine gene function and treat diseases of genetic basis. In addition, gene transfer provides the basis for high-level protein expression, used by molecular researchers to study protein function and to produce new protein drugs. The introduction of genes into animals can also produce useful animal models of human diseases.

Viral vectors, such as adenoviral or retroviral vectors, have been used to introduce foreign DNA into cells with high efficiency. These vectors include adenoviral vectors and retroviral vectors.

The wild type adenovirus genome is approximately 36 kb, of which up to 30 kb can be replaced with foreign DNA. There are four early transcriptional units (E1, E2, E3 and E4), which have regulatory functions, and a late transcript, which codes for structural proteins. Replication-defective vectors have been produced, which have an essential region of the virus (e.g. E1) deleted. Other genes (e.g. E3 or E4) can be also deleted in the replication-deficient vectors. These additional gene deletions increase the capacity of the vector to carry exogenous nucleic acid sequences. The E2 region can also be deleted in a replication-defective vector; this type of vector is known as a "mini Ad," "gutted vector," or "gutless vector." In order to utilize these "gutless vectors", a helper cell line, (e.g. 293 cells), is needed to provide necessary proteins for virus packaging. Although adenoviral vectors, including gutless vectors, can infect both dividing and non-dividing cells, they generally do not stably integrate into the cellular genome (Dales and Chardonnet, 1973; Greber et al., 1997; Greber et al., 1996; Harui et al., 1999; Schaack et al., 1990).

In an alternative strategy, retroviruses, such as Moloney murine leukemia virus (MoMLV), have been used to introduce genes into cells. Retroviruses are RNA viruses that, when they infect cells, convert their RNA into a DNA form, which is then integrated into the cellular genome. The integrated provirus can produce RNA from a promoter located in the long terminal repeats (LTRs), which are DNA repeats located at the end of the integrated genome. Retroviral DNA vectors are plasmid DNAs which contain two retroviral LTRs, and a gene of interest inserted in the region internal to these LTRs. The retroviral vector can be packaged by packaging cell lines, containing the gag, pol, and env genes, which provide all the viral proteins required for capsid production and the virion maturation of the vector.

A retroviral vector integrates into the cellular genome once it is introduced into cells, thereby stably transfecting the cells. However, most retroviruses except the Human Immunodeficiency Virus (HIV) can transfect only cells that are dividing; retroviral vectors cannot be used to introduce nucleic acid into non-dividing cells. Efficient integration of MoMLV requires the viral integrase (IN) and CATT sites located at the termini of the viral 3' and 5' long terminal repeats (LTRs). Both the 5' and 3'LTRs are considered necessary for the integration (Asante-Appiah and Skalka, 1997; Brown, 1997; Donehower and Varmus, 1984; Goff, 1992; Panganiban and Temin, 1983; 1984; Roth et al., 1989; Schwartzberg et al, 1984).

Hybrid vectors have also been developed in order to overcome disadvantages of single viral vectors (Caplen et al., 1999; Feng et al., 1997; Ramsey et al., 1998; Torrent et al., 1998; Vile et al., 1998). For example, multiple adenoviral vectors were constructed to provide different transcomplementing functions able to support the production of a recombinant retroviral vector in vivo. One disadvantage to this approach is that individual cells must be infected by more than one adenovirus. Additionally, since the recombinant vector produced in vivo is a retrovirus, cell division is still required for the virus to enter the nucleus and become integrated. This latter fact is a significant drawback to use of such a system with cells that are terminally differentiated and non-dividing.

The high-efficiency transfer of genes is also of use in vivo. Over the past decade a new approach to the treatment of disease has been developed using genes as therapeutic agents. The goal of gene therapy is to deliver DNA into the body for the treatment of an array of inherited and acquired diseases. Since the first clinical gene therapy protocol for severe combined immunodeficiency disease started in September 1990, more than 300 clinical protocols have been approved worldwide. Clinical experience suggests that gene therapy has the potential to treat a broad range of human diseases, with a low risk of adverse reactions. However, the efficiency of gene transfer and expression in vivo is still relatively low (Donehower, et al., *Proc. Natl. Acad. Sci. USA* 81: 6461–6465, 1984.

The gene delivery system is frequently the limiting factor for successful gene therapy. Ideally, a gene therapy vector should efficiently and safely deliver therapeutic genes to the target tissues, and should produce a therapeutic amount of gene product for the appropriate time, without requiring any complementing functions supplied in trans. Unfortunately, none of the vector systems presently in use meet all of these requirements.

Both retroviruses (e.g., Moloney Murine Leukemia Virus, MoMLV), and adenoviruses, have been used for human gene therapy. Experience has demonstrated that although a retroviral vector such as a MoMLV vector is a minimal safety risk, its low titer and low gene transfer efficiency make it most suitable for ex vivo use. In addition, as described above, MoMLV can integrate into the genome only in dividing cells.

In contrast to a retrovirus, the transport of an adenovirus to the nucleus is rapid in both dividing and non-dividing cells in vivo. However, an immune response can be generated against the adenoviral proteins produced by an adenoviral vector. In general, the "gutless vectors" induce less of an immune response than other adenoviral vectors. In addition, although adenoviruses can be produced at very high titers and may infect cells with high efficiency, they integrate into the cell genome only at very low frequency, which results in unstable gene expression.

Thus a need exists for a single vector which can be used to stably introduce nucleic acid into both dividing and non-dividing cells, which can be used both in vitro and in vivo.

SUMMARY OF THE INVENTION

An adenoviral vector is provided that includes a single retroviral LTR and a transgene. Although the adenoviral vector does not include two retroviral LTRs, the adenoviral vector still can integrate into the genome of a host cell, and the transgene is expressed.

An adenovirus is provided that includes adenoviral capsid proteins and an adenoviral vector comprising adenoviral Inverted Terminal Repetitions (ITRs) flanking a packaging signal and a single retroviral LTR operably linked to a nucleic acid sequence of interest, wherein the adenoviral vector does not include the retroviral structural proteins, and wherein the adenoviral vector is packaged in the adenoviral capsid proteins, thereby producing infective adenovirus.

An adenoviral vector is provided that includes two adenoviral ITRs, wherein the two adnoviral ITRs flank a packaging signal and a single retroviral LTR operably linked to a nucleic acid sequence of interest, wherein the adenoviral vector does not include a nucleic acid sequence encoding the retroviral structural proteins and wherein the adenoviral vector does not include a second retroviral LTR.

In one embodiment, a method for transforming a cell is provided. The method includes contacting the cell with an adenoviral vector including two adenoviral ITRs, wherein the two adnoviral LTRs flank a single retroviral LTR operably linked to a nucleic acid sequence of interest. The adenoviral vector does not include a nucleic acid sequence encoding the retroviral structural proteins and wherein the adenoviral vector does not comprise a second retroviral LTR. Contacting the cell with the adenoviral vector results in transformation of the cell.

In another embodiment, a method is provided for introducing a transgene into a cell with a single viral vector. The method includes contacting the cell with an adenoviral vector including a 5' adenoviral ITR 5' of both a single retroviral LTR and a transgene, and a 3' adenoviral ITR 3' of both the single retroviral LTR and the transgene. The adenoviral vector does not comprise a second LTR, and the adenoviral vector is replication defective. The cell is not able to produce viral particles, and no other viral vector is introduced into the cell.

In a further embodiment, a method is provided for preventing or treating a disorder in a subject. The method includes introducing into a cell of the subject an therapeutically effective amount of an adenoviral vector including adenoviral ITRs flanking a single retroviral LTR operably linked to a nucleic acid sequence of interest. The adenoviral vector does not include the retroviral structural proteins, and the introduction results in the genetic transformation of the cell and expression of the nucleic acid sequence of interest. In this method, the expression of the nucleic acid sequence of interest results in alleviating a symptom of the disorder or preventing the disorder.

A pharmaceutical composition is also provided. The composition includes an adenoviral vector including a 5' adenoviral ITR 5' of both a single retroviral LTR and a transgene, and a 3' adenoviral ITR 3' of both the single retroviral LTR and the transgene wherein the adenoviral vector does not include a second LTR, and wherein the adenoviral vector is replication defective, and a pharmaceutically acceptable carrier.

The foregoing and other objects, features, and advantages of the invention will become more apparent from the following detailed description of several embodiments which proceeds with reference to the accompanying figures.

BRIEF DESCRIPTION OF THE FIGURES

FIG. 2A is a schematic diagram of Ad5'LTR-luc, which contains 2.7 kb of the MoMLV 5'LTR, a luciferase reporter, and the SV40 polyadenylation sequence downstream of the luciferase cDNA. FIG. 2B is a schematic diagram of AdCMV-luc, a first generation adenoviral vector and has been reported previously (Wang et al., 1999; Zheng et al., 2000). This vector does not include a LTR.

FIG. 3A is a bar graph of the reverse transcriptase activity in supernatants from HSY and A5 cells 10 days post-infection with Ad5'LTR-luc (20 pfu/cell), and in positive control samples (MoMLV standard). SPA represents scintillation proximity assay results and corresponds with reverse transcriptase activity. FIG. 3B is a bar graph of luciferase activity in HSY and A5 cells 10 days post-infection with Ad5'LTR as in A. Data shown are average values of duplicate determinations from one of two comparable experiments.

FIG. 4A is a schematic diagram of the design of PCR primers used to detect MoMLV integrase and reverse transcriptase genes. FIGS. 4B, 4C, 4D and 4E show results from the PCR assays.

FIG. 5A is a bar graph demonstrating luciferase activity in the salivary epithelial cell lines HSY, A5 and HSG following infection. FIG. 5B is a bar graph demonstrating luciferase activity in mononuclear cells (Mono) and macrophages (Macr) from normal human peripheral blood, and hippocampus neurons (Hipp) from rat brain (B) following infection. Luciferase activity was assayed 24 hr after infection. FIG. 5C is a bar graph of cellular luciferase activity in a A5 cell clone (#13; see FIG. 6) infected with Ad5'LTR-luc, which was randomly selected, and cultured without selection medium for 9 months. Luciferase activity was measured at 1 month and 9 month time points. FIG. 5D is a graph of luciferase expression after in vivo infection. A time course of luciferase activity in rat submandibular gland after retrograde ductal infusion of virus ($2\times10^9$ pfu/gland) is shown. Data presented are the mean±SD for results of triplicate determinations in cell lines, and separate tissue samples from each of three rats in vivo at each time point.

FIG. 6A is a schematic diagram of the design of PCR primers used to detect a 5'LTR breakpoint (PCR 1), a downstream 5'LTR site (PCR 2) and the presence of the luciferase cDNA (PCR 3) in Ad5'LTR-luc. Target cells or tissues were infected with Ad5'LTR-luc and the PCR assays performed as described in FIG. 6B is a digital image of the control assays performed. FIG. 6C is a digital image of the results obtained with 10 clones of A5 cells (numbered) that were infected with Ad5LTR-luc, and samples from three rats infected with Ad5'LTR-luc in the submandibular glands. Note that samples from two A5 clones appeared to exhibit a disruption of the 5'LTR (i.e.

clones 5 and 2; loss of the PCR 1 amplicon), as did two rat submandibular gland samples (1, 2) obtained at 9 weeks post-infection.

Figure 7:
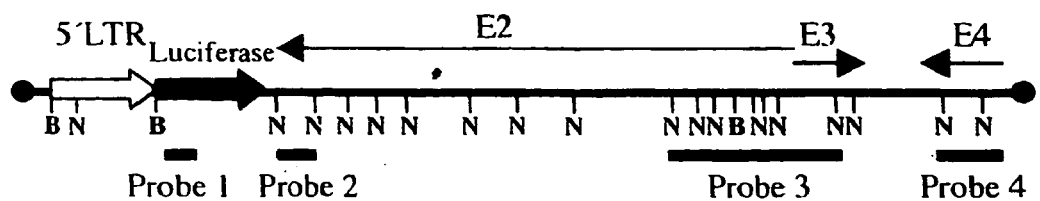
Figure 7:
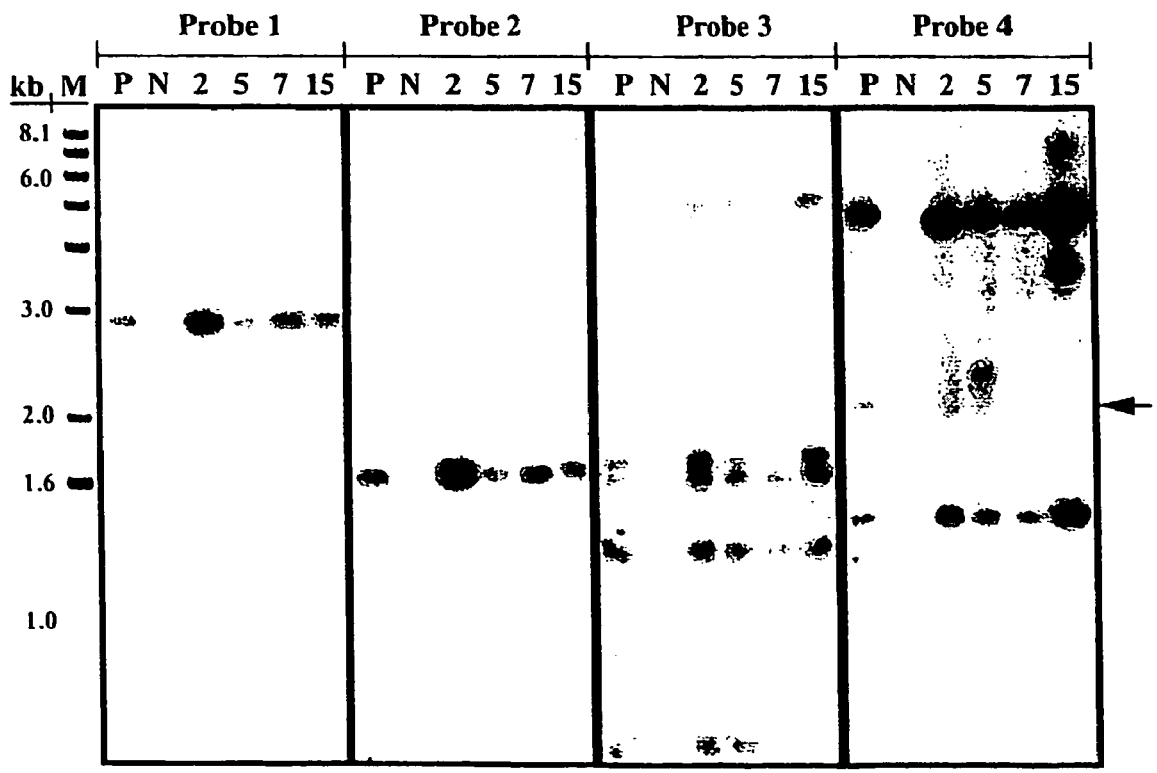

FIG. 7 shows the Southern hybridization for the detection of integration and breakpoints with Bam HI/Nco I digestion of DNA from A5 cell clones. DNA samples were obtained from cloned A5 cells (2, 5, 7, 15) infected with Ad5'LTR-luc, or uninfected cells (panel B; N). Positive control (P) DNA was from uncloned cells infected with Ad5'LTR-luc 3 days before harvesting DNA. Each lane represents 15 µg of DNA applied and hybridized on the same blot by sequential hybridization, after stripping, with probes 1, 2, 3 or 4. FIG. 7A shows a diagram of Bam HI (B) and Nco I (N) target site localization and probe position in Ad5'LTR-luc. FIG. 7B is a digital image of southern hybridization results. Note that there was no break (altered band size) seen in all cloned cells with probes 1, 2 and 3. However, the second band seen with the positive control using probe 4 was absent in all cloned cells, indicating that there possibly was break in this area (arrow).

Figure 8:
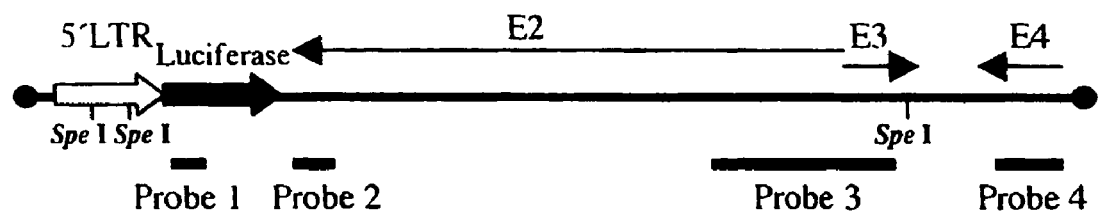
Figure 8:
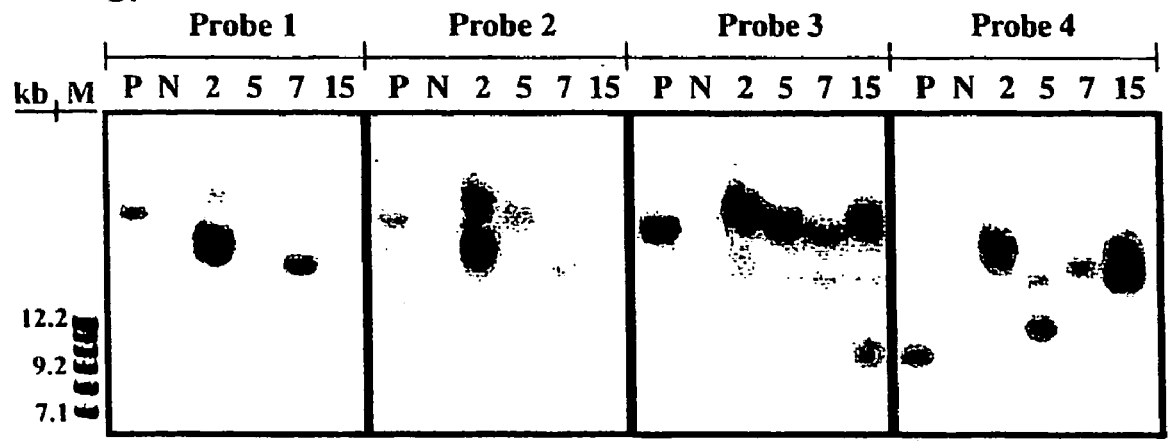

FIG. 8 shows the Southern hybridization for the detection of integration and breakpoints with Spe I digestion of DNA from A5 cell clones. All samples were the same as in FIG. 7. Samples were digested with Spe I and hybridized on the same blot by sequential hybridization, after stripping, with probes 1, 2, 3 or 4. FIG. 8A is a diagram to show enzyme target site localization and probe position in Ad5'LTR-luc. FIG. 8B is a digital image of Southern hybridization results. All cloned cells had unique positive bands with each probe compared to the positive control. Use of probes 1–3 show that the same DNA band (the uppermost band) was recognized by each. However, there was a second band with samples from clones #2 and #7 using probes 1 and 2. It appeared that for each of these clones the same band was hybridized to both probes 1 and 2, suggesting that there was a breakpoint in E2A region. All cloned cell DNA samples showed different hybridization bands from the positive control when probe 4 was used.

Figure 9:
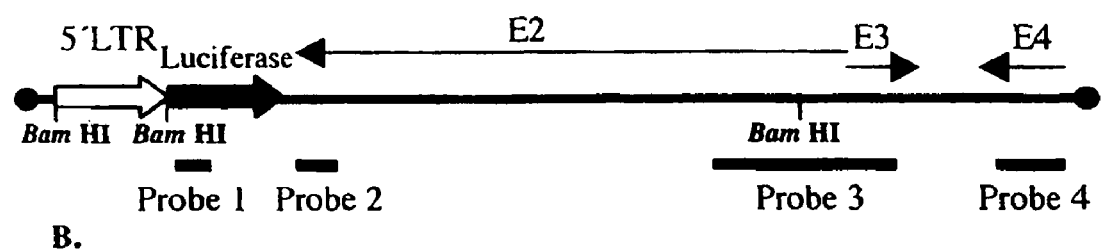
Figure 9:
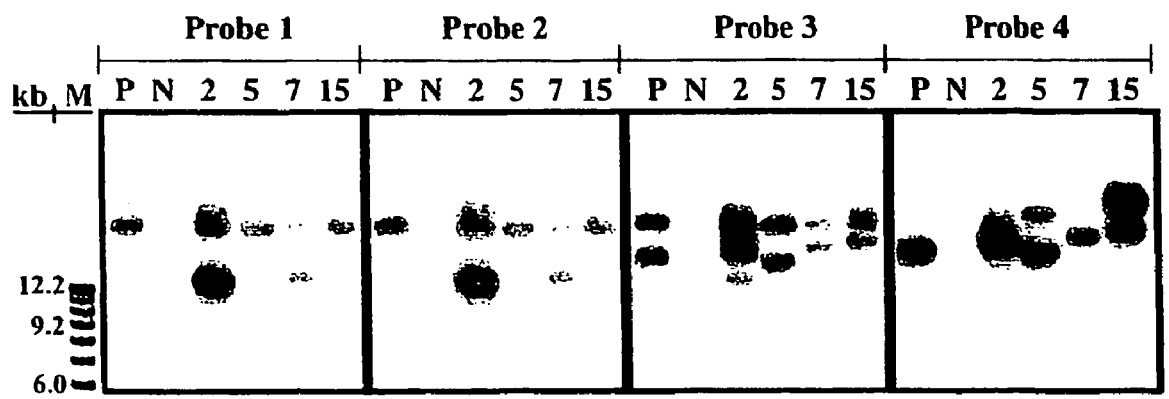

FIG. 9 shows the Southern hybridization for the detection of integration and breakpoints with Bam HI digestion of DNA from A5 cell clones. All samples were as in FIG. 7. Samples were digested with Bam HI and hybridized on the same blot by sequential hybridization, after stripping, with probes 1, 2, 3 or 4. FIG. 9A is a schematic diagram to show enzyme target site localization and probe position in Ad5'LTR-luc. FIG. 9B shows Southern hybridization results. Note that the hybridization results were similar by probes 1 and 2 with these samples. Using probe 3, the uppermost band was similar to the uppermost band found with probes 1 and 2. This suggests that there were no breaks in the region between these three probes. The lower bands hybridized to probe 3 in cloned cells, and results obtained from using probe 4, indicate that there was a break in the probe 4 region.

Figure 10:
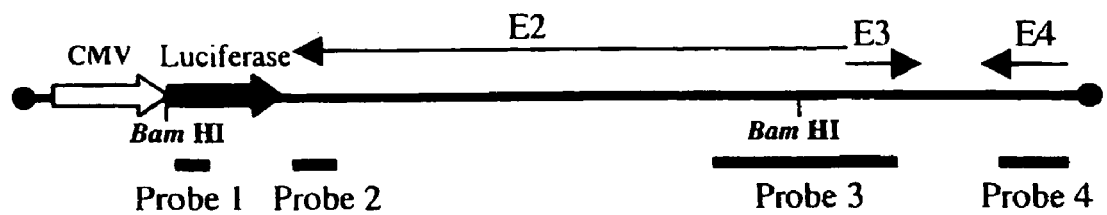
Figure 10:
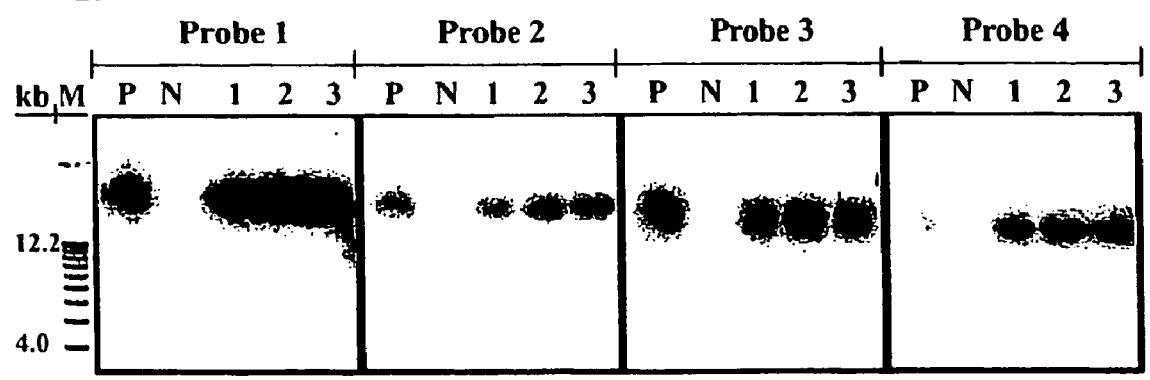

FIG. 10 shows the Southern hybridization of DNA samples from cells infected with AdCMV-luc. DNA samples were obtained from A5 cells (1, 2, 3) infected with AdCMV-luc, individually isolated and grown in vitro for 1 month, or from uninfected cells (N). Positive control (P) DNA was from uncloned cells infected with AdCMV-luc 3 days before harvesting DNA. Each lane represents 15 µg of DNA applied and hybridized on the same blot by sequential hybridization, after stripping, with probes 1, 2, 3 or 4. FIG. 10A shows a diagram of Bam HI target site localization and probe position in AdCMV-luc. FIG. 10B shows a digital image of Southern hybridization results. There were no differences in the pattern of bands seen in all isolated cells with probes 1, 2, 3 and 4, from those seen with the positive control sample. The uppermost band seen with probe 3, corresponds to the single band seen with probes 1 and 2. Similarly, the lower band seen with probe 3 corresponds the single band seen with probe 4.

Figure 11:
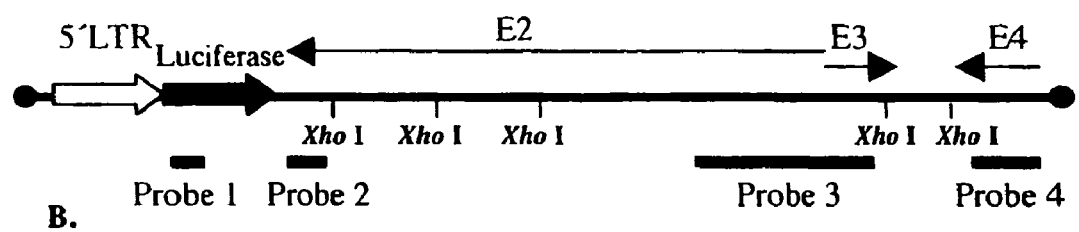
Figure 11:
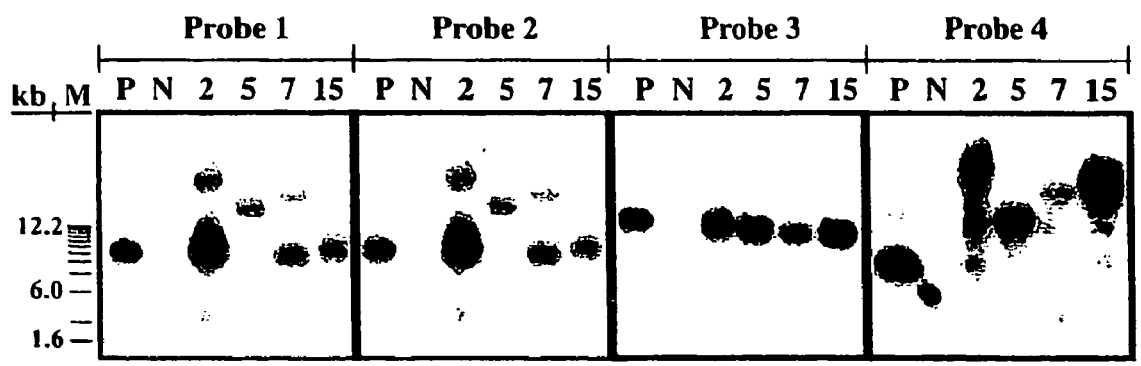

FIG. 11 shows the Southern hybridization for the detection of integration and breakpoints with Xho I digestion of DNA from A5 cell clones. All samples were as in FIG. 7. Samples were digested with Xho I and hybridized on the same blot by sequential hybridization, after stripping, with probes 1, 2, 3 or 4. FIG. 11A is a schematic diagram to show enzyme target site localization and probe position in Ad5'LTR-luc. FIG. 11B is a digital image of Southern hybridization results. The same pattern was seen with probes 1 and 2, suggesting there were no breaks between these two probes, but rather a break upstream of probe 1. Probe 3 hybridized to the same bands in all cloned cells and the positive control indicating no break in this region. Probe 4 results show different sized bands for all cloned cell DNA samples, consistent with there being a break in E4 region.

Figure 12:
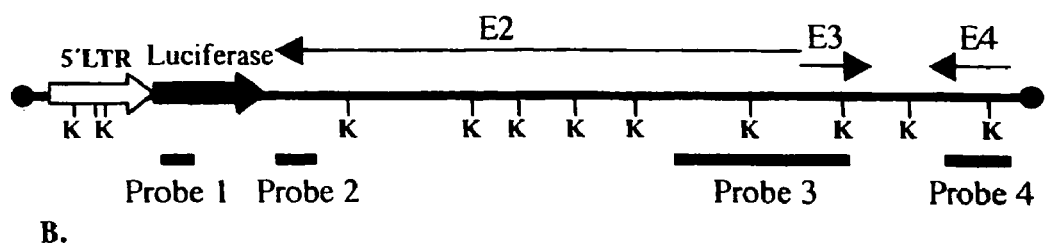
Figure 12:
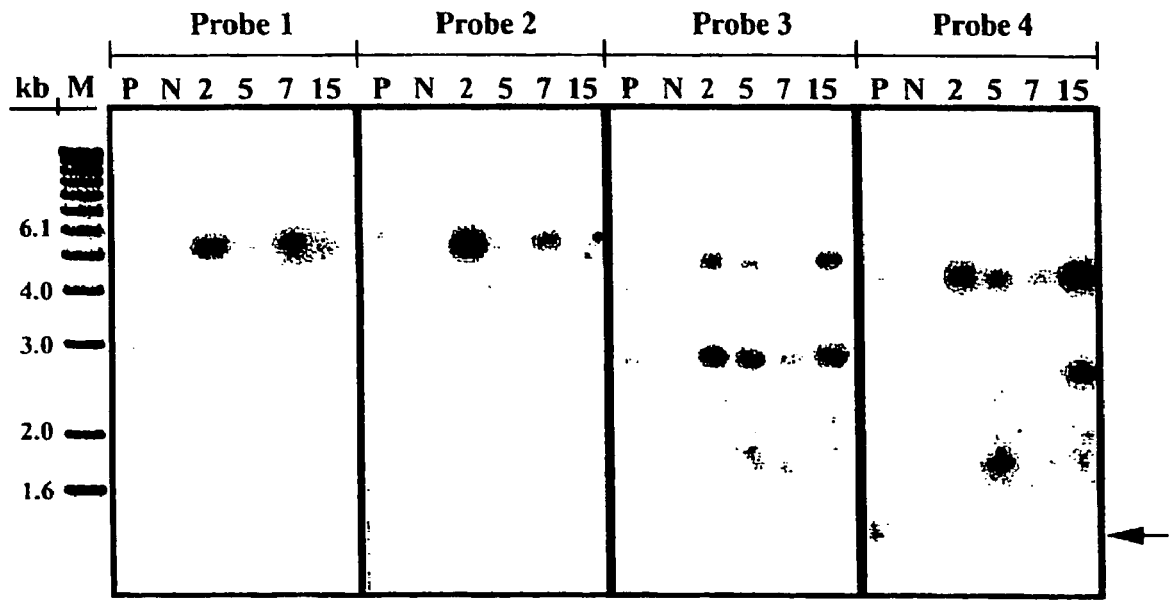

FIG. 12 shows Southern hybridization for the detection of integration and breakpoints with Kpn I digestion of DNA from A5 cell clones. All samples were as in FIG. 7. Samples were digested with Kpn I and hybridized on the same blot by sequential hybridization, after stripping, with probes 1, 2, 3 or 4. FIG. 12A is a diagram to show enzyme target site localization and probe position in Ad5'LTR-luc. FIG. 12B is a digital image of Southern hybridization results. The same pattern was seen with probes 1 and 2, suggesting there were no breaks between these two probes, but rather a break upstream of probe 1. Probe 3 hybridized to the same bands in all cloned cells and the positive control indicating no break in this region. The probe 4 results show that a different hybridized band pattern was seen for all cloned cell DNA samples, indicating that there was break in this area (arrow).

Figure 13:
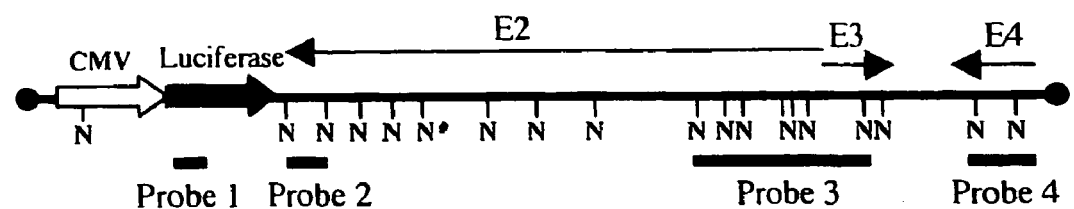
Figure 13:
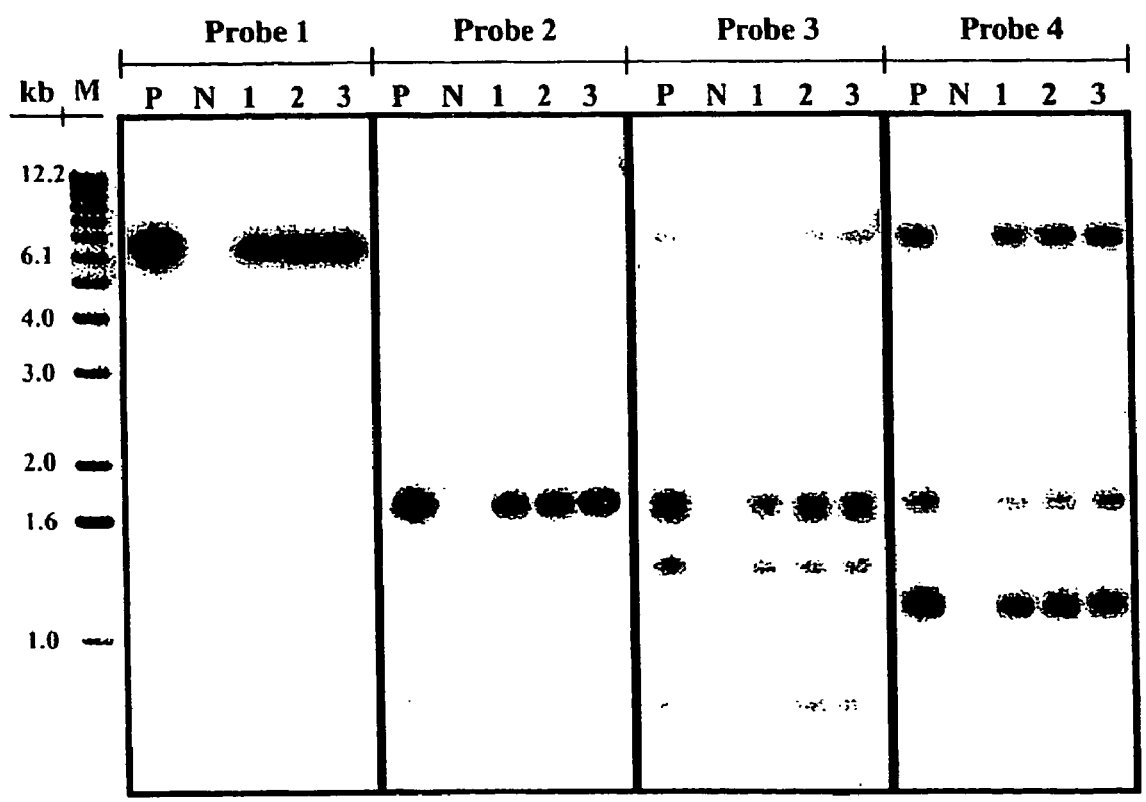

FIG. 13 shows the Southern hybridization of DNA samples from cells infected with AdCMV-luc. DNA samples were obtained from A5 cells (1, 2, 3) infected with AdCMV-luc, individually isolated and grown in vitro for 1 month, or from uninfected cells (panel B; N). Positive control (P)-DNA was from uncloned cells infected with AdCMV-luc 3 days before harvesting DNA. Each lane represents 15 µg of DNA applied and hybridized on the same blot by sequential hybridization, after stripping, with probes 1, 2, 3 or 4. FIG. 13A shows a diagram of Nco I (N) target site localization and probe position in Ad5'LTR-luc. FIG. 13B is a digital image of Southern hybridization. There are no differences in band size seen in all amplified cells hybridized with probes 1, 2, 3 and 4, compared to the results obtained with the positive control sample.

Figure 14:
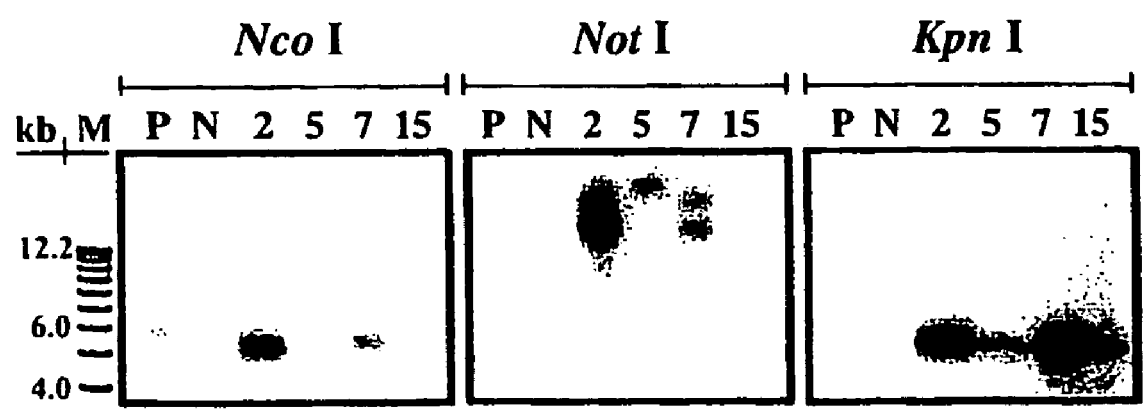

FIG. 14 is a digital image of the Southern hybridization for the detection of breakpoints in 5'LTR. Nco I, Not I and Kpn I digestion individually was performed on DNA from A5 cell clones. All of the resulting blots were hybridized with probe 1. All positive bands from the cloned cells were different from that seen with the positive control, consistent with breaks in the 5'LTR.

Figure 15:
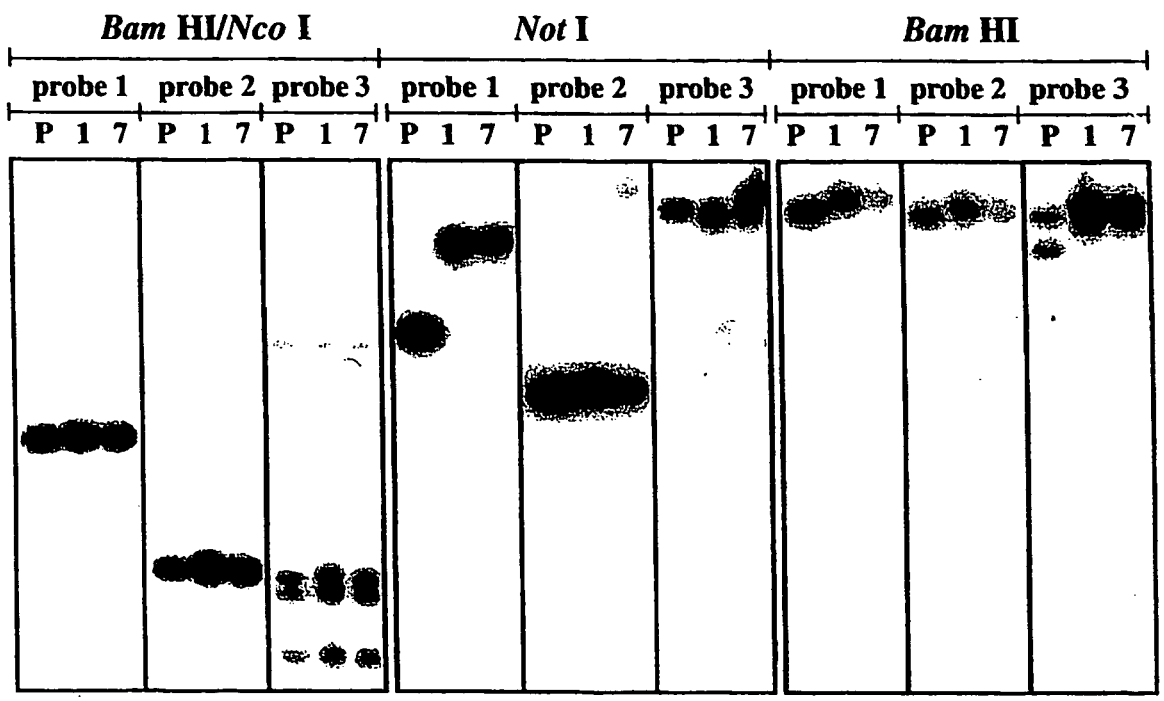

FIG. 15 is a digital image of the southern hybridization for the detection of long term stable integration in vitro. One A5 cell clone (#13) was infected with Ad5'LTR-luc and was randomly selected and cultured without selection media. Genomic DNA samples obtained at two time points after infection, 1 and 7 months, were used in these experiments. The samples were digested with either Bam HI/Nco I, Not I or Bam HI, and hybridized on the same blot by sequential hybridization, after stripping, with probes 1, 2 or 3. The results show that Ad5'LTR-luc was integrated into the genome, and that this integration did not change over the time period.

Figure 16:
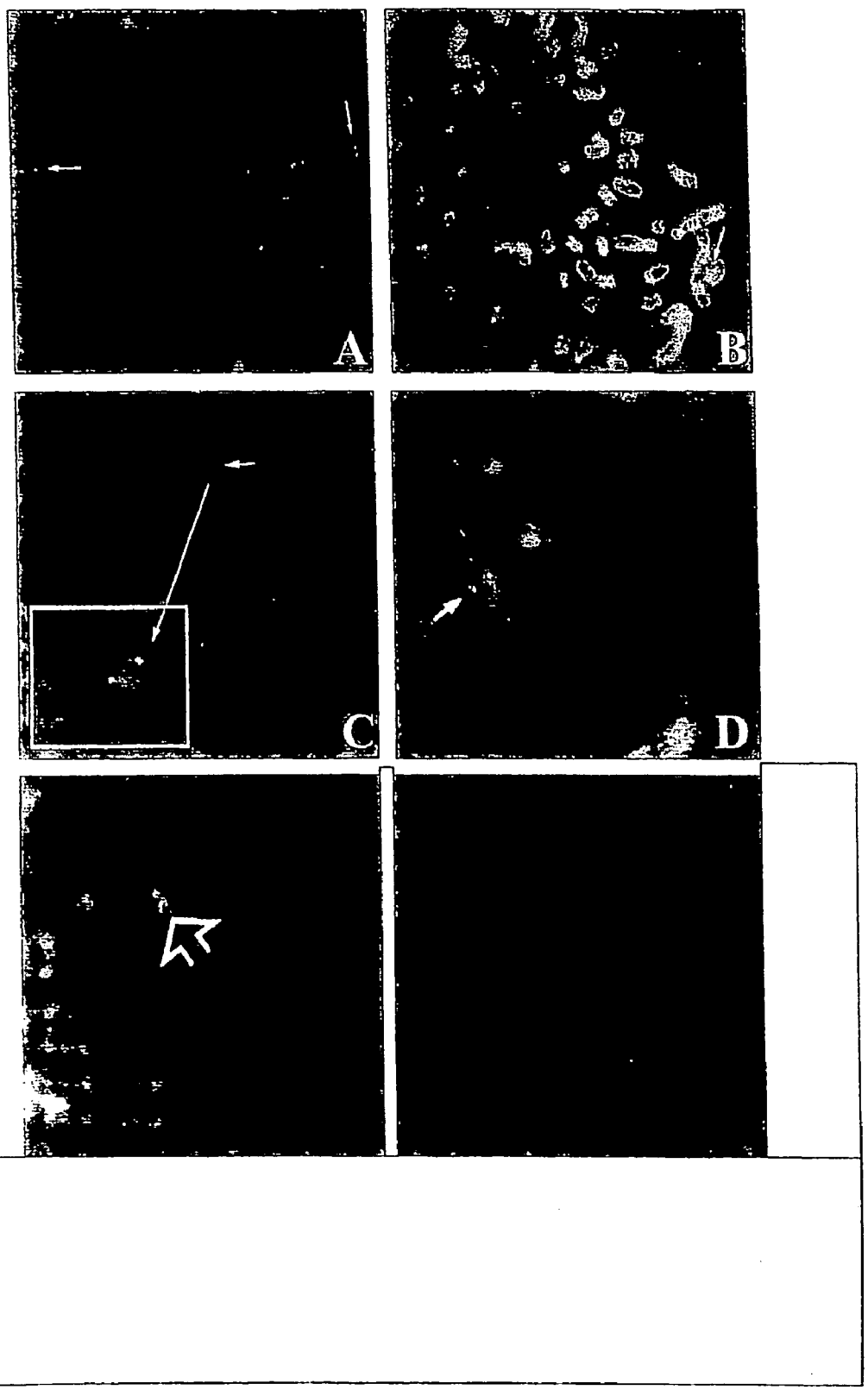

FIG. 16 is a digital image of FISH analyses of A5 and HSY cells for the detection of integration. Panels A, B and C came from A5 cells one week after infection with Ad5'LTR-luc. FIG. 16A is a digital image of two positive allelic spots on two different chromosomes by using FISH probe 1, i.e. the LTR plus luciferase. FIG. 16B is a digital image of two positive allelic spots on a chromosome using the E2B probe (probe 2). FIG. 16C is a digital image of a two probe hybridization result (two color detection), with probe 1 (light blue color) and probe 3 (E2A/E3 probe; red color), co-localized on the same chromosome. FIG. 16D is a digital image of cloned A5 cells (clone #13) 7 months post-infection with Ad'LTR-luc with integration detected by probe 1 (arrow showing two positive spots on the chromosome). FIG. 16E is a digital image of HSY cells one week after infection with Ad5'LTR-luc. Two positive allelic spots are shown on a chromosome using FISH probe 1. FIG. 16F is a digital image of HSY cells one week after infection with AdCMV-luc using pACCMV-luc as a probe. No evidence for integration is seen.

DETAILED DESCRIPTION OF SEVERAL EMBODIMENTS

Definitions

The following definitions and methods are provided to better define the present invention, and to guide those of ordinary skill in the art in the practice of the present invention. It must be noted that as used herein and in the appended claims, the singular forms "a", "an", and "the" include plural referents unless the context clearly dictates otherwise. Thus, for example, reference to "a cell" includes a plurality of such cells and reference to "the vector" includes reference to one or more vectors and equivalents thereof known to those skilled in the art, and so forth.

Unless defined otherwise, all technical and scientific terms used herein have the same meaning as commonly understood to one of ordinary skill in the art to which this invention belongs.

Adenovirus: An family of icosahedral (20-sided) viruses that contain DNA. Two genuses, Mastadenovirus and Aviadenovirus are included in the adenovirus family. While there are over 40 serotype strains of adenovirus, most of which cause benign respiratory tract infections in humans, subgroup C serotypes 2 or 5 are predominantly used as vectors. The life cycle does not normally involve integration into the host genome, rather an adenovirus replicates as episomal elements in the nucleus of the host cell and does not insert into the genome. A "adenoviral vector" is a vector derived from publicly available adenoviral DNA. At a minimum, an adenoviral vector includes the inverted terminal repetitions of an adenovirus.

Animal: Living multicellular vertebrate organisms, a category which includes, for example, mammals and birds.

Antisense, Sense, and Antigene: Double-stranded DNA (dsDNA) has two strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional or physical binding assays. Binding may be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method which is widely used, because it is so simple and reliable, involves observing a change in light absorption of a solution containing an oligonucleotide (or an analog) and a target-nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Capsid: The protein covering, or outer coat, of a virus particle. The capsid is a protein coat that covers the nucleoprotein core or nucleic acid of a virion. The capsid generally shows icosahedral symmetry and in some viruses (not adenoviruses) is enclosed in an envelope. The capsid is built up of subunits (some integer multiple of 60, the number required to give strict icosahedral symmetry) that self assemble in a pattern typical of a particular virus. The subunits are often packed, in smaller capsids, into 5 or 6 membered rings (pentamers or hexamers) that constitute the morphological unit (capsomere). A capsid is required for viral infection of a cell.

Envelope polypeptide or Env: An "env" polypeptide is a retroviral "envelope" protein which encodes the surface (SU) glycoprotein and the transmembrane (TM) protein of the virion. The SU glycoprotein and the TM protein form a complex that interacts specifically with cellular receptors. In one embodiment, a "portion" of a env protein refers to at least 15 consecutive amino acids of a env protein sequence. In one embodiment, a "portion" of an env protein refers to at least 25 consecutive amino acids of an env protein sequence. In yet another embodiment, a "portion" of an env protein refers to at least 35 consecutive amino acids of an env protein sequence.

Essential Gene: A gene required for viral replication, packaging or infection. Deletion of an essential gene renders a virus replication defective. For example, in an adenovirus, E1 and E2 are essential genes.

Gene, Genome, and Genetic Target: The terms "gene," "genome," and "genetic target" include both DNA and RNA. Generally, a gene is a sequence of DNA or RNA that codes for a protein. A "target" sequence is a sequence to which an antisense or sense oligonucleotide or analog specifically hybridizes.

Group Specific Antigen Polypeptide or Gag: A "gag" protein is a retroviral "group specific antigen" polypeptide which is proteolytically processed into the mature proteins MA (matrix), CA (capsid), and NC (nucleocapsid), and other proteins that are numerically designated.

Functional Deletion: A mutation in a sequence that has an effect equivalent to deletion of the sequence, for example eliminating the function of a packaging signal or an essential gene product by a deletion, insertion, or substitution.

Functionally Equivalent: Sequence alterations, in either the transfer or packaging vector sequences, that yield the same results as described herein. Such sequence alterations can include, but are not limited to, conservative substitutions, deletions, mutations, frameshifts, and insertions. In an adenoviral vector deleted for E1 of the invention, deletions in an another gene, such as E4, are functionally equivalent to a similar vector including an E3 deletion. In addition, alterations of the adenoviral vector sequence which yield enhanced encapsidation of the transfer vector genome, are functionally equivalent to the transfer vector of the invention.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Figure 2:
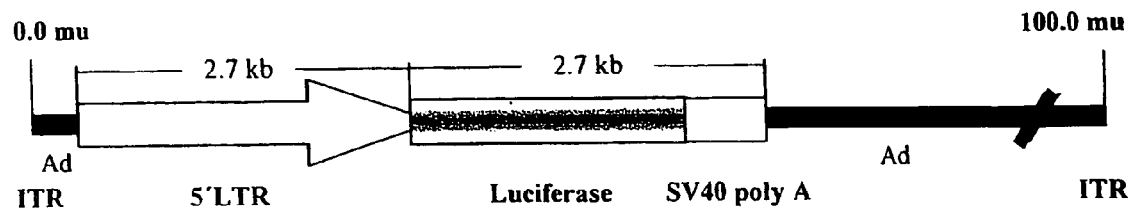
FIG. 2 is a schematic diagram of the structure of Ad5'LTR-luc and AdCMV-luc.
Figure 2:
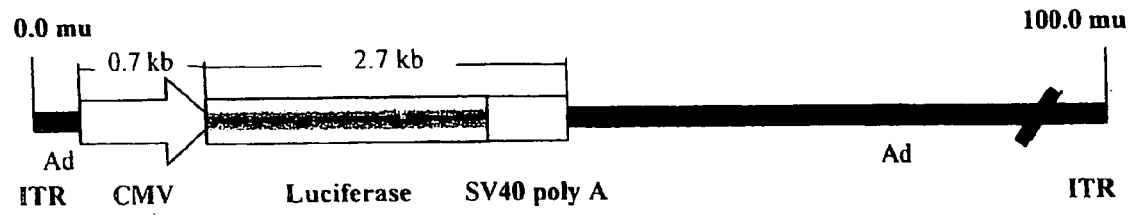

Hybrid Adenoviral Vector: An adenoviral vector that includes a sequence from a retrovirus incorporated into the adenoviral vector. Specific non-limiting examples of hybrid adenoviral vectors are Ad5'LTR-luc (FIG. 2) and AdCMV-luc (FIG. 2). In one embodiment, a single LTR from a retrovirus, (e.g. MoMLV) are inserted in an adenovirus 5 vector. The adenoviral 5 vector can also be further modified. In one embodiment the adenviral vector is replication defective. In one embodiment, the adenoviral vector is replication-defective vector as it has been modified to delete the function of an essential adenoviral gene. Specific, non-limiting examples of essential adenoviral genes are E1 and E3.

Infective: A virus or vector is "infective" when it transduces a cell, replicates, and (without the benefit of any complementary virus or vector) spreads progeny vectors or viruses of the same type as the original transducing virus or vector to other cells in an organism or cell culture, where the progeny vectors or viruses have the same ability to reproduce and spread throughout the organism or cell culture. Thus, for example, a nucleic acid encoding an adenoviral particle is not infective if the nucleic acid cannot be packaged (e.g. if the adenoviral particle lacks a packaging site), even though the nucleic acid can be used to transfect a cell. Similarly, an adenoviral nucleic acid packaged by an adenoviral particle is not infective if it does not encode the adenoviral capsid proteins that it is packaged in.

Integration: A virus "integrates" into cellular DNA when the nucleic acid of the virus is incorporated into the cellular genome (i.e. into a chromosome).

Inverted Terminal Repetition (ITR): A sequence found in adenovirus located the end of each strand, these sequences are inverted repeats. When the virus is denatured the repeats enable the formation of "panhandle" structures of 100–140 bp from the single nucleic acid strands.

Isolated: An "isolated" nucleic acid has been substantially separated or purified away from other nucleic acid sequences and in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

Long Terminal Repeat or LTR: An "LTR" is a "long terminal repeat" that is generated as a DNA duplex at both ends of the retrovirus when a retrovirus integrates into a host genome. The 5' LTR includes a U3, R, and U5 nucleic acid element. The 3' LTR also includes U3, R, and U5 nucleic acid element. In a replication competent retrovirus, LTRs also contain an active RNA polymerase II promoter which allows transcription of the integrated provirus by host cell RNA polymerase II to generate new copies of the retroviral RNA genome.

Figure 1:
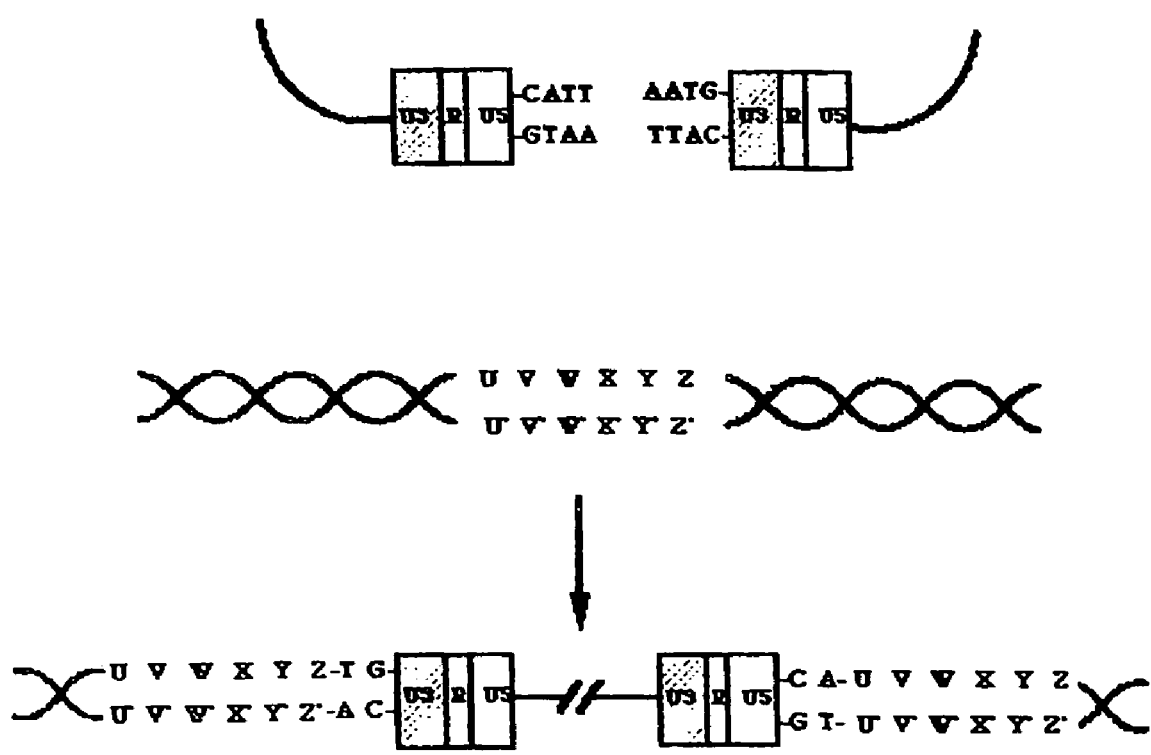
FIG. 1 is a diagram of the integration of a retroviral vector, in which two LTRs are required.

An integrated retrovirus has two LTRs, one at the 5' end and one at the 3' end of the viral genome. The "5' LTR" is located at the 5' end of the retroviral DNA, and the "3' LTR" is located at the 3' end of the retroviral DNA (FIG. 1).

Mammal: This term includes both human and non-human mammals. Similarly, the term "subject" includes both human and veterinary subjects.

Nucleic acid sequence (or polynucleotide): A deoxyribonucleotide or ribonucleotide polymer in either single or double stranded form, and unless otherwise limited, encompasses known analogues of natural nucleotides that hybridize to nucleic acids in a manner similar to naturally occurring nucleotides, and includes polynucleotides encoding full length proteins and/or fragments of such full length proteins which can function as a therapeutic agent. A polynucleotide is generally a linear nucleotide sequence, including sequences of greater than 100 nucleotide bases in length.

Nucleotide: "Nucleotide" includes, but is not limited to, a monomer that includes a base linked to a sugar, as in DNA and RNA, or a base linked to an amino acid, as in a peptide nucleic acid (PNA). A nucleotide is one monomer in a polynucleotide. A nucleotide sequence refers to the sequence of bases in a polynucleotide.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Packaging cell: A cell that provides packaging functions in trans for a gene introduced into a cell with a transfer vector, but which does not encapsidate its own viral RNA.

Packaging Signal: A complex signal, also known as "φ", that is important for the packaging of virus in viral particles.

Packaging Vector: Packaging vector nucleic acids lack the nucleic acids necessary for packaging of a DNA corresponding to the packaging vector nucleic acid into an adenoviral capsid. That is, packaging vector nucleic acids are not themselves encapsidated in the viral particles which they encode, i.e. they are not infective. The packaging vector optionally includes all of the components necessary for production of viral particles, or optionally includes a subset of the components necessary for viral packaging. For instance, a packaging cell may be transformed with more than one packaging vector, each of which has a complementary role in the production of an adenoviral particle.

Two (or more) adenoviral-based packaging vectors are "complementary" when they together encode all of the functions necessary for adenovirus packaging, and when each individually does not encode all of the functions necessary for packaging. For example, when two vectors transduce a single cell and together they encode the information for production of adenovirus packaging particles, the two vectors are "complementary." The use of complementary vectors increases the safety of any packaging cell made by transformation with a packaging vector by reducing the possibility that a recombination event will produce an infective virus.

Adenoviral packaging cell lines are cells including nucleic acid molecules that encode adenoviral capsid proteins which can be used to form adenoviral particles. The adenoviral particles are competent to package target adenovirus which has a packaging site.

Polymerase or Pol: A "pol" protein is a retroviral reverse transcriptase, which contains both DNA polymerase and associated RNAse H activities, and Integrase (IN). Pol mediates replication of the viral genome in vivo. The ends of the newly synthesized linear double-stranded viral DNA are recognized and two nucleotides from the 3' end of each strand are removed. These DNA ends are joined to a target DNA at random sites.

Polypeptide: Any chain of amino acids, regardless of length or post-translational modification (e.g., glycosylation or phosphorylation). In one embodiment, a polypeptide can be a "marker" polypeptide, which is used to identify cells that express the polypeptide. A marker polypeptide can be detected using methods known to one of skill in the art, including enzymatic assays and assays utilizing antibodies (e.g. ELISA or immunohistochemistry). Specific non-limiting examples of a marker protein are luciferase, green fluorescent protein (GFP), or beta-galactosidase. In another embodiment, a polypeptide is a "therapeutic" polypeptide, which can be used to alleviate or relieve a symptom of a disorder. Specific, non-limiting examples of therapeutic polypeptides are cytokines or immunomodulators, hormones, neurotransmitters, or enzymes.

Probes and primers: A probe comprises an isolated nucleic acid attached to a detectable label or reporter molecule. Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive contiguous nucleotides from a DNA sequence will anneal to a target with a higher specificity than a corresponding primer of only 15 contiguous nucleotides. Thus, in order to obtain greater specificity, probes and primers may be selected that comprise 20, 25, 30, 35, 40, 50 or more contiguous nucleotides.

Purified: The term purified does not require absolute purity; rather, it is intended as a relative term. Thus, for example, a purified protein preparation is one in which the protein is more pure than the protein in its natural environment within a cell. For example, a preparation of a protein is purified such that the protein represents at least 50% of the total protein content of the preparation.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Replication defective: A virus is replication defective if it cannot replicate in a host cell.

Retrovirus: Any virus in the family Retroviridae. These viruses have similar characteristics, specifically they share a replicative strategy. This strategy includes as essential steps reverse transcription of the virion RNA into linear double-stranded DNA, and the subsequent integration of this DNA into the genome of the cell. All native retroviruses contain three major coding domains with information for virion proteins: gag, pol and env. In one embodiment, a retrovirus is an avian sarcoma and leukosis virus, a mammalian B-type virus, a Murine leukemia-related virus, a Human T-cell leukemia-bovine leukemia virus, a D-type virus, a lentivirus, or a spumavirus. In another embodiment, the virus is a Rous sarcoma virus, a mouse mammary tumor virus, a human T-cell leukemia virus, a Mason-Pzifer monkey virus, a human immunodeficiency virus, a human foamy virus, or a Molony Leukemia Virus. A retrovirus generally contains three genes known as "gag," "pol," and "env."

Sequence identity: The similarity between two nucleic acid sequences, such as an antisense sequence and a gene, or two amino acid sequences, is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, *Methods in Molec. Biology* 24: 307–331, 1988; Higgins and Sharp, *Gene* 73:237–244, 1988; Higgins and Sharp, *CABIOS* 5:151–153, 1989; Corpet et al., *Nucleic Acids Research* 16:10881–90, 1988; Huang et al., *Computer Applications in BioSciences* 8:155–65, 1992; and Pearson et al., *Methods in Molecular Biology* 24:307–31, 1994

The NCBI Basic Local Alignment Search Tool (BLAST) (Altschul et al., *J. Mol. Biol.* 215:403–410, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at the NCBI (BLAST) website. A description of how to determine sequence identity using this program is available at the NCBI (BLAST) website.

Homologs of a protein, such as a marker or a therapeutic protein, is typically characterized by possession of at least 70% sequence identity counted over the full length alignment with the disclosed amino acid sequence using the NCBI Blast 2.0, gapped blastp set to default parameters. Such homologous peptides will more preferably possess at least 75%, more preferably at least 80% and still more preferably at least 90% or 95% sequence identity determined by this method. When less than the entire sequence is being compared for sequence identity, homologs will possess at least 75%, 85%, 90% or 95% sequence identity over short windows of 10–20 amino acids. Methods for determining sequence identity over such short windows are described at the NCBI (BLAST) website. One of skill in the art will appreciate that these sequence identity ranges are provided for guidance only; it is entirely possible that strongly significant homologs or other variants could be obtained that fall outside of the ranges provided.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at the NCBI (BLAST) website.

One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The Tm is the temperature (under defined ionic strength and pH) at which 50% of the target sequence remains hybridized to a perfectly matched probe or complementary strand. Conditions for nucleic acid hybridization and calculation of stringencies can be found in Sambrook et al. (*Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to an encoding sequence will typically hybridize to a probe based on either an entire encoding sequence or selected portions of the encoding sequence under wash conditions of 2×SSC at 50° C.

Supernatant: The culture medium in which a cell is grown. The culture medium includes material from the cell. If the cell is infected with a virus, the supernatant can include viral particles.

Target sequence: "Target sequence" is a portion of ssDNA, dsDNA or RNA that, upon hybridization to a therapeutically effective antisense oligonucleotide or oligonucleotide analog, results in the inhibition of expression of the target sequence. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount: An amount of a therapeutic protein or antisense molecule effective to inhibit or treat a disease. Although this amount varies depending on the severity and nature of a condition being treated, examples of effective amounts are tissue concentrations that are effective to provide relief of a symptom.

Transgenic animal: Any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. This molecule can be integrated within the animal's chromosomes, or can be present as extrachromosomally replicating DNA sequences, such as might be engineered into yeast artificial chromosomes.

The term "transgenic animal" includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

RNA: All types of ribonucleic acid (RNA), including viral genomic RNA and mRNA.

Therapeutically Effective Oligonucleotides: Characterized by their ability to inhibit the expression of a gene of interest. Complete inhibition is not necessary for therapeutic effectiveness. Therapeutically effective oligonucleotides are characterized by their ability to inhibit the expression of the gene of interest. Inhibition is defined as any reduction in expression seen when compared to production in the absence of the oligonucleotide or oligonucleotide analog. Additionally, some oligonucleotides will be capable of inhibiting the expression of a gene of interest by at least 15%, 30%, 40%, 50%, 60%, or 70%, or more.

Therapeutically effective oligonucleotides are additionally characterized by being sufficiently complementary to nucleic acid sequences encoding a gene of interest. As described herein, sufficient complementary means that the therapeutically effective oligonucleotide can specifically disrupt the expression of a gene, and not significantly alter the expression of other genes.

Transduced and Transformed: A virus or vector "transduces" or "transfects" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: An exogenous gene or heterologous nucleic acid sequence supplied by a vector. In one embodiment the transgene encodes a marker protein which can be detected using methods known to one of skill in the art. Specific non-limiting examples of a marker protein are luciferase, green fluorescent protein (GFP), or beta-galactosidase. In another embodiment, the transgene encodes a therapeutic protein, which can be used to alleviate or relieve a symptom of a disorder. Specific, non-limiting examples of therapeutic proteins are cytokines or immunomodulators, hormones, neurotransmitters, or enzymes. In another embodiment, the transgene encodes a therapeutically effective oligonucleotide (e.g. an antisense oligonucleotide), wherein expression of the oligonucleotide inhibits the expression of a target nucleic acid sequence. In a further embodiment, the transgene encodes an antisense nucleic acid or a ribozyme. In yet another embodiment, the transgene encodes an enzyme. Specific, non-limiting examples of enzymes are kinases, phosphorylases, deaminases, or any enzyme that converts pro-drugs to an active form of the drug.

The transgene can have the native regulatory sequences operably linked to the transgene (e.g. the wild-type promoter, found operably linked to the gene in a wild-type cell). Alternatively, a heterologous promoter can be operably linked to the transgene. In yet another embodiment, the viral LTR can be used to express the transgene.

A transgene can also include a large nucleic sequence. In one embodiment the nucleic acid encodes several polypeptides. In one embodiment the transgene can be up to 20 Kb of nucleic acid sequence. In another embodiment the transgene can include up to 10 Kb of nucleic acid sequence. In yet another specific non-limiting example the transgene is from about 10 bases to about 20 Kb of nucleic acid sequence.

Transfer (or Shuttle) vector: A vector which shuttles a gene, but does not include all of the components necessary for production of adenoviral particles.

Variant oligonucleotides and variant analogs: A variation of an oligonucleotide or an oligonucleotide analog is an oligomer having one or more base substitutions, one or more base deletions, and/or one or more base insertions, so long as the oligomer substantially retains the activity of the original oligonucleotide or analog, or has sufficient complementarity to a target sequence.

A variant oligonucleotide or analog may also hybridize with the target DNA or RNA, under stringency conditions as described above. A variant oligonucleotide or analog also exhibits sufficient complementarity with the target DNA or RNA of the original oligonucleotide or analog as described above.

Vector: A nucleic acid molecule as introduced into a host cell, thereby producing a transformed host cell. A vector may include nucleic acid sequences that permit it to replicate in the host cell, such as an origin of replication. A vector may also include sequences encoding one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. A vector may be a viral vector, derived from a virus, such as an adenoviral vector.

Additional definitions of common terms in molecular biology may be found in Lewin, B. "Genes V" published by Oxford University Press.

Viral Vectors and Viruses

Hybrid adenoviral vectors that provide highly efficient gene transfer to both dividing and non-dividing host cells have been developed. The hybrid adenoviral vectors integrate into the cellular genome such that a transgene is integrated into the cellular genome and is stably expressed. In one embodiment, the hybrid adenoviral vectors are replication-defective, as they are deficient in the production of an essential gene product. One specific, non-limiting example of an essential adenoviral gene is E1. Another specific, non-limiting example of replication defective adenoviral vectors are E1/E2/E3/E4 deficient vectors.

Other strategies have required the use of multiple adenoviral vectors to provide transcomplementing functions to support the production of a recombinant vector. The present system is unique in that all the required functions are present in the hybrid adenoviral vector itself. In addition, in one embodiment, no viral particles are produced once the hybrid adenoviral vector enters the host cell.

The adenoviral vector includes a single retroviral LTR within the adenoviral vector. Thus, a second retroviral LTR is not included in the adenoviral vector. In one embodiment, the adenoviral vector can also include a portion of a retroviral envelope protein. The retroviral LTR and the envelope polypeptide can be derived from any known retrovirus. In one specific, non-limiting example, a retroviral LTR and an envelope sequence from MoMLV is utilized. In another embodiment, a packaging sequence from the retrovirus (e.g. MoMLV) is also included in the adenoviral vector. In a further embodiment, the retroviral packaging sequence is located downstream of this 5'LTR.

In one embodiment, the single retroviral LTR included in the adenoviral vector is a 5' LTR. In this embodiment, the adenoviral vector does not include a 3' LTR. In one embodiment, the 5' LTR is an MoMLV LTR. In one specific, non-limiting example, the adenoviral vector includes about 2.7 kb of nucleic acid sequence of MoMLV, which includes the 5' LTR. This sequence includes the 5' LTR, the packaging signal, and a portion of the MoMLV envelope polypeptide. In another embodiment, about 1.0 kb of MoMLV including the 5'LTR is utilized in a hybrid adenoviral vector. This sequence includes the 5' LTR and a portion of the viral envelope protein, but does not include the packaging signal. In one specific, non-limiting example the 1.0 kb of MoMLV is from about base pair 1155 to about base pair 2168 (a fragment 1,013 base pairs in length). In yet another embodiment, about 0.5 kb of MoMLV including the 5' LTR is utilized in the hybrid adenoviral vector.

In another embodiment, the single retroviral LTR included in the adenoviral vector is a 3' LTR. In this embodiment, the adenoviral vector does not include a 5' LTR. In one specific, non-limiting example, the 3' LTR is a MoMLV LTR. For example, about 1.0 kb of MoMLV nucleic acid sequence, including the 3' LTR, is utilized in the hybrid adenoviral vector. The sequence includes the 3' LTR and a portion of the viral envelope protein. In a further embodiment, about 0.5 kb of MoMLV including a 3' LTR is utilized in the hybrid adenoviral vector.

The adenoviral vector includes at a minimum two adenoviral ITRs. In one embodiment, the adenoviral vector also includes a nucleic acid sequence encoding a transgene (see below). The transgene is operably linked in that the LTR facilitates integration of the transgene. In one embodiment, the transgene is also operably linked to the LTR such that expression of the transgene is controlled by the LTR. In another embodiment, expression of the transgene is controlled by additional or other regulatory elements, such as a heterologous promoter, operably linked to the transgene. The promoter can be a constitutive or an inducible promoter. Specific non-limiting examples of promoters of use are CMV, RSV, SV40, or tissue specific promoters (e.g., amylase, kallikrein, insulin, immunoglobulin, propmoters, etc.). Exemplary constructs and plasmids including these constructs are shown in FIG. 2.

The adenoviral vectors including a single retroviral LTR achieve stable expression of the transgene as they integrate into the cellular genome. Stable transgene expression is achieved in both dividing and non-dividing cells. The adenoviral vectors can be used to infect any cell of interest, either in vivo or in vitro.

In one embodiment, the adenoviral vector is replication defective. In a specific, non-limiting example, the E1 region is deleted in a replication-defective adenoviral vector. In another specific non-limiting example, the E1, E2, E3, and/or E4 region of the adenovirus is deleted (e.g. a "mini Ad," "gutted vector," or "gutless vector" see Example 7).

The hybrid adenoviral vector can be packaged in adenoviral capsid proteins, thereby producing infective adenovirus. Any method known to one of skill in the art for producing adenoviral capsid proteins, and for packaging adenoviral vectors can be utilized with the hybrid adenoviral vectors of the invention. For example, one specific, non-limiting method of packaging hybrid adenoviral vectors is the use of 293 cells.

Transgenes

The transgene can be any sequence of interest. In one embodiment, the transgene is a nucleic acid sequence encoding a marker (e.g. luciferase (luc), β-galactosidase (β-gal), or green fluorescent protein (GFP)). In another embodiment, the transgene encodes a therapeutic polypeptide. A therapeutic polypeptide is any polypeptide which can be used to treat a disorder in a subject or cell. Specific, non-limiting examples of therapeutic polypeptides include cytokine and immunomodulators, hormones, and neurotransmitters. In a subject or cell deficient for a specific polypeptide, a therapeutic polypeptide can be that specific polypeptide, can be a variant of that specific polypeptide, or can be another polypeptide that serves the same function in the subject or cell. Specific non-limiting examples of therapeutic polypeptides of use with the invention include, but are not limited to, IL-10, IL-6, EPO, growth hormone (GH), alpha antitrypsin), and alpha-galactosidase A.

In one embodiment of the present invention, the hybrid retrovirus can include a transgene that encodes an antisense molecule, which includes antigene molecules. Antisense and sense molecules include oligonucleotides that interfere with expression of DNA or RNA. In one aspect of the present invention, the antisense or sense molecules can bind to the target RNA, or otherwise interfere with the translation of the target RNA. In another aspect of the invention, the antisense molecule induces Rnase H-mediated RNA degradation, or inhibits RNA polymerase II. In another aspect of the invention, the antisense molecule binds to the target DNA and disrupts transcription.

For instance, antisense or antigene molecules can have complementary nucleotide sequences to the target DNA or RNA. These complementary nucleotide sequences can specifically hybridize to the target DNA or RNA by Watson-Crick base pair formation or Hoogsteen base pair formation.

Expression of the transgene in transfected cells can be evaluated by a variety of techniques including ELISA, Southern blot, Northern blot and other standard protein assays which allow one to determine that the transgene is being expressed (for example assaying for the conversion of L-dopa to L-dopamine after transfecting cells with the AADC gene). Transfected cells can be analyzed for cellular RNA by extraction of the RNA by standard methods, and by measurement of absorbance of light at set wavelengths. Northern blot and slot-blot hybridization can be used to quantify RNA.

Without further elaboration, it is believed that one skilled in the art can, using this description, utilize the present invention to its fullest extent. The following examples are illustrative only, and not limiting of the remainder of the disclosure in any way whatsoever.

EXAMPLES

Example 1

Material and Methods

Recombinant Viral Vectors

The replication-deficient recombinant adenoviral vectors used are based on the adenovirus type 5 (Ad5) genome. E1 deletion was achieved by recombination of the pAC shuttle plasmid (a generous gift of Dr. C. Newgard) with pJM17 (Microbix Biosystems Inc., Toronto, Ontario, Canada) (Becker et al., 1994). 2.7 kb of the 5'LTR from MoMLV were removed by EcoR I from the plasmid pXT1 (Stratagene, La Jolla, Calif.)(Boulter and Wagner, 1987). As removed from pXT1, this 2.7 kb fragment includes (5' to 3' direction) part of the envelope gene (1.5 kb), the 5'LTR (0.57 kb), and the packaging sequence (0.63 kb)(also see FIG. 5A). Not I linkers were added to both ends of this fragment, and the fragment ligated into pAC (the LTR sequences were placed in the deleted E1 adenoviral region). Thus, this construct did not contain any gag or pol sequences from MoMLV. The luciferase (luc) cDNA fragment was removed from the plasmid pGL2-Basic (Promega, Madison, Wis.) and ligated downstream of the 5'LTR fragment. The luciferase gene was driven by the 5'LTR promoter. This plasmid was termed pAC5'LTR-luc. The plasmid pACCMV-luc contained the CMV promoter/enhancer and luciferase cDNA without any retroviral elements (Wang et al., 1999; Zheng et al., 2000). The recombinant adenoviruses (FIG. 1), Ad5'LTR-luc and AdCMV-luc, were generated by homologous recombination of pAC5'LTR-luc and pACCMV-luc, respectively, with pJM17 in 293 cells (Becker et al., 1994), and verified by Southern hybridization analyses and luciferase enzymatic assays.

Cell Culture

The human mononuclear cells and macrophages were obtained from the peripheral blood of normal volunteers. The cells were separated on Ficoll Hypaque, and washed twice with PBS. The mononuclear cells were cultured in suspension in RPMI 1640 with 10% human serum for 2 weeks before infection. The macrophages were adherent to the bottom of the flask after the mononuclear cells were cultured for one week. The medium was replaced twice a week for 25 days before infection.

Hippocampus neurons, which were kindly provided by Dr. Z. G. Jiang (NIMH, NIH, Bethesda, Md.), were obtained from Tac:N(SD)fBR rats at 18 gestational days. Hippocampus tissue was cut into 1 mm cubes and then triturated by using fire-restricted Pasteur pipettes to achieve single cells. The cells were seeded at a density of 40,000/well in a 96-well plate, and cultured in neurobasal medium supplemented with 1×B27 and 2 mM glutamine for two weeks before infection. This method yields cultures containing 95–98% hippocampal neurons (Dr. Z. G. Jiang, personal communication).

The HSY ductal cell line was obtained from a human parotid adenocarcinoma (Yanagawa et al., 1986) and was grown in a mixture of 50% Dulbecco's MEM and 50% Ham's F 12 media. The ductal epithelial A5 cell line was derived from rat submandibular gland (Brown et al., 1989) and grown in McCoy's 5A medium. The HSG cell line was obtained from an irradiated human submandibular gland (Shirasuna et al., 1981), and was grown in DMEM/F12 medium, as above. For in vitro experiments, all cells were infected with Ad5'LTR-luc at 50 pfu/cell, unless otherwise stated.

One randomly selected A5 cell clone, obtained by limiting dilution, was cultured without special selection media for >9 months. The doubling time for A5 cells is between 18 and 24 hours. Therefore, this cell clone was passaged though more than 200 cell cycles.

Animal Experiments

All experimental protocols were approved by the NIDCR Animal Care and Use Committee, and the NIH Biosafety Committee, and all procedures were conducted in accordance with the IASP standards for the treatment of animals. Male Wistar rats (250–350 g, ~3 months old) were used for in vivo studies. Rats were anesthetized with ketamine (36 μg/g body weight) and xylazine (3.2 μg/g body weight) injected intraperitoneally. For infection of rat submandibular glands, viruses (2×10$^9$ pfu/gland) were injected by retrograde ductal instillation (Mastrangeli et al., 1994).

Luciferase Assay

Cells and tissues were lysed, and homogenized as necessary, in cell lysis buffer (Promega) for 15 minutes. Fifty microliters of the cell lysate were added to 100 μl of luciferase substrate, and light output was measured with a luminometer. Results are expressed as relative light units (RLU) per cell number or per μg protein.

Reverse Transcriptase Assay

HSY cells and A5 cells were infected with Ad5'LTR-luc (50 pfu/cell). The supernatants from infected cell cultures were harvested at day 10. MoMLV reverse transcriptase was obtained from GIBCO BRL Life Technologies (Rockville, Md.). The reverse transcriptase assay was carried out using a Quan-T-RT assay system from Amersham Life SCIENCE (Buckinghamshire, England).

PCR Assays

The genomic DNA used in the PCR assays was extracted with either a Wizard Genomic DNA Purification Kit (Promega) or a Non-Organic DNA Extraction kit (Intergen, Purchase, N.Y.). PCR assays used the same general procedures as reported by us previously (Zheng et al., 2000). Briefly, 200–1000 ng of template DNA were used in each PCR reaction. To determine if the MoMLV integrase and reverse transcriptase contaminated our adenoviral preparations, four primers to amplify integrase fragments were employed:

IN.F (5'-GGGGGGATCCAATCATCACCCTAGACT-TGTGCACAAGCTTTG CAGGTCTCAGTG-3')(SEQ ID NO:1, Dotan et al., 1995);

Inf15 (5'-CAAGTCAACGCCAGCAAGTCTG-3') (SEQ ID NO:2);

IN.B (5'-GACTTGTGCACAAGCTTTGCAGGTCT-CAGTG-3')(SEQ ID NO:3, Dotan et al., 1995); and INb44 (5'-CATGTCAGGGTCAGGGAAGTTTAC-3') (SEQ ID NO:4).

Four primers to amplify reverse transcriptase fragments were also employed:

RTf11 (5'-TGGAGAGATCCAGAGATGGGAATC-3') (SEQ ID NO:5);

RTf15(5'-CACCCTGTTTGATGAGGCACTG-3') (SEQ ID NO:6);

RTb35(5'-GGGCAGTTAGAAGAGCTTGCTTG-3') (SEQ ID NO:7); and RTb47(5'-CCAAGGTCCCAGTTTTTGCG-3') (SEQ ID NO:8).

Figure 3:
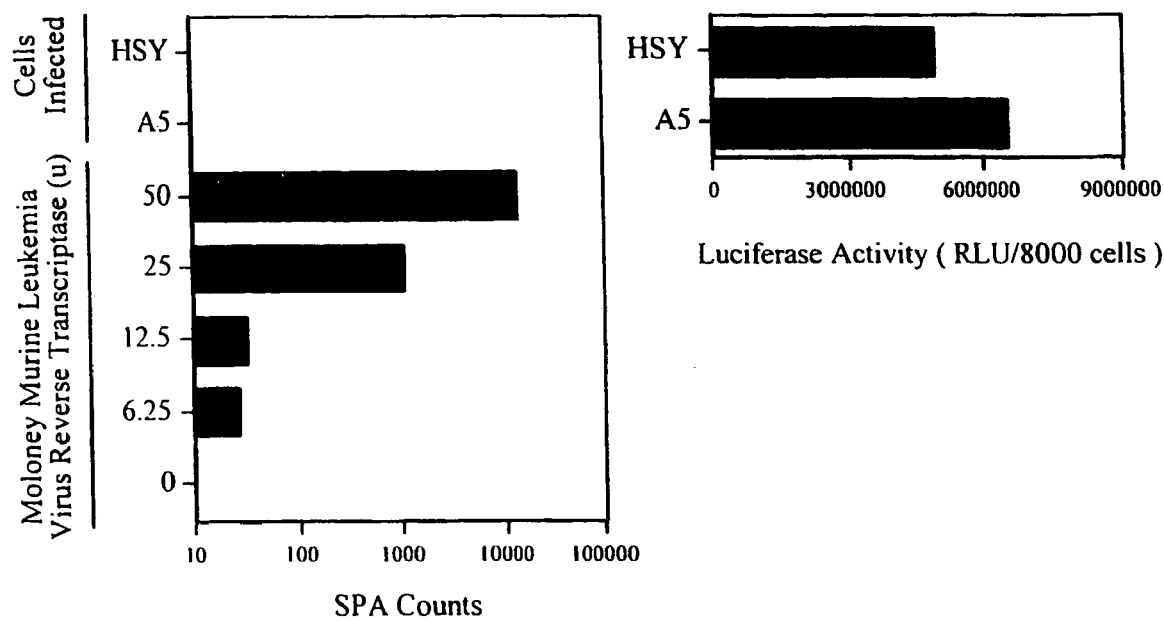
FIG. 3 is a series of bar graphs showing reverse transcriptase and luciferase activity in Ad5'LTR-luc infected cells.
Figure 4:
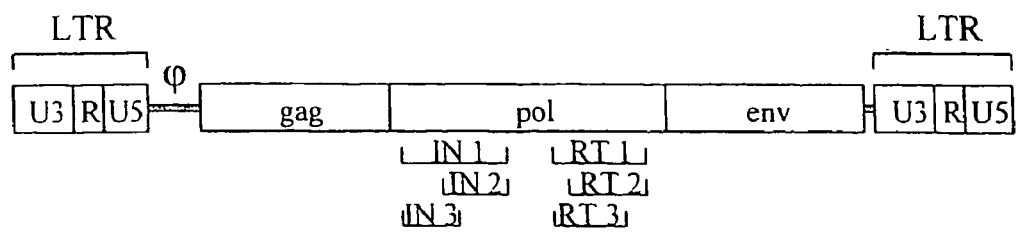
FIG. 4 is a schematic diagram and photographs showing the strategy used in and results from PCR assays to screen for possible contamination of Ad5'LTR-luc with integrase and reverse transcriptase genes.
Figure 4:
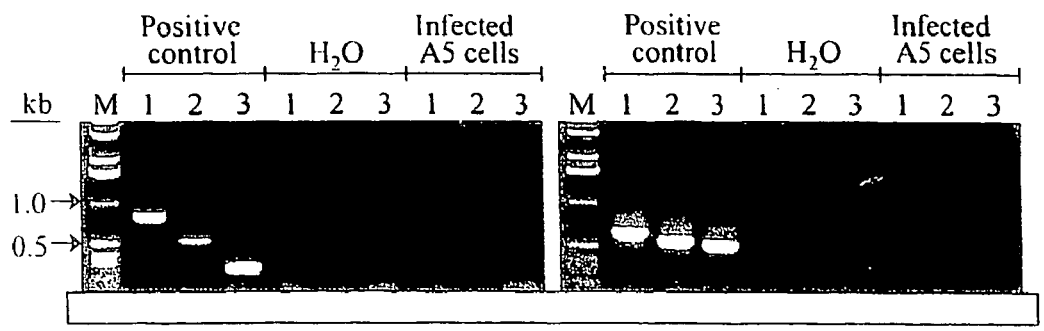
Figure 4:
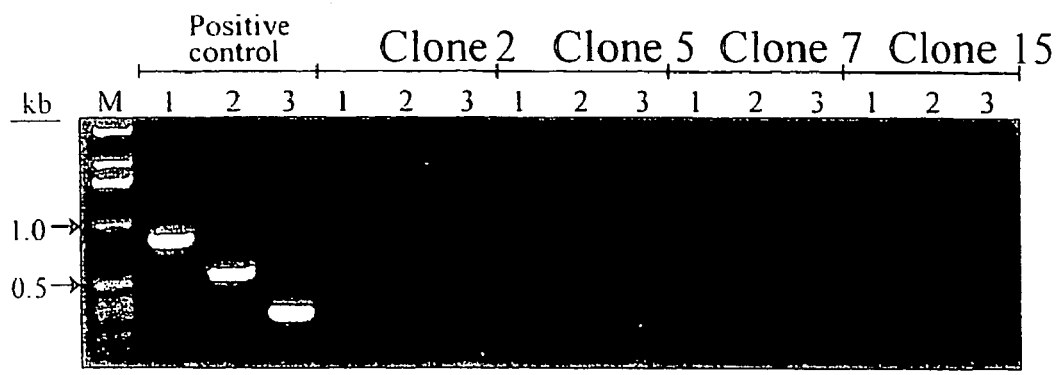
Figure 4:
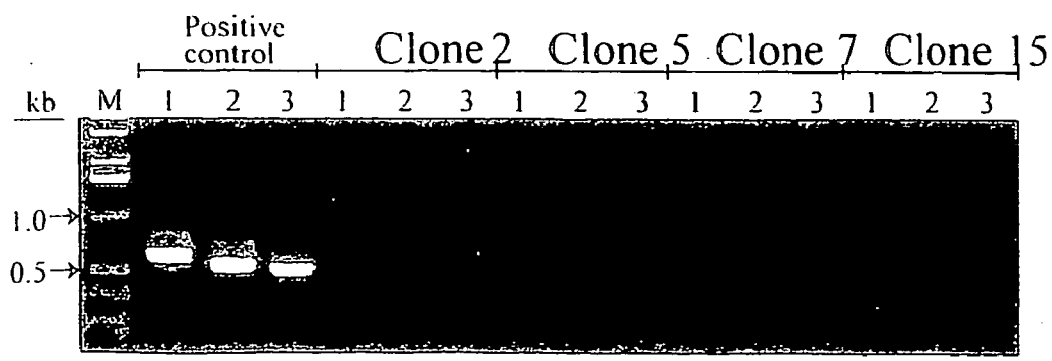

IN.F and Inb44 produced a 857 base pair (bp) product (IN 1) (see FIG. 4). INf15 and Inb44 produced a 554 bp product (IN 2) (FIG. 4). The amplicon IN 3 (303 bp) was obtained by IN.F and IN.B (FIG. 4). RTf11 and TRb47 produced a 650 bp product (RT 1) (FIG. 3). RTf15 and RTb47 produced a 576 bp product (RT 2) (FIG. 4). The amplicon RT 3 was obtained by RTf11 and RTb35 (FIG. 4). For these experiments, the positive DNA sample used was genomic DNA extracted from RetroPack PT67 cells (Clontech Laboratories, Inc. Palo Alto, Calif.), which is an amphotropic packaging cell line for MoMLV based vectors. This cell line expresses the MoMLV pol proteins.

Figure 6:
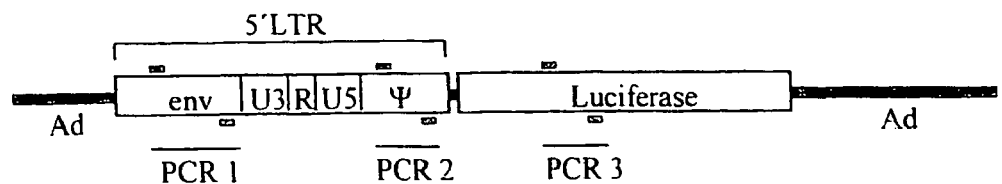
FIG. 6 shows the PCR assay to screen for the possible integration of Ad5'LTR-luc.
Figure 6:
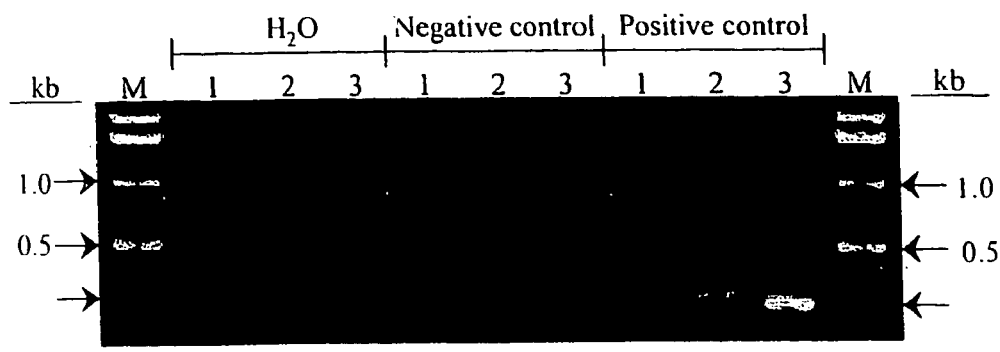
Figure 6:
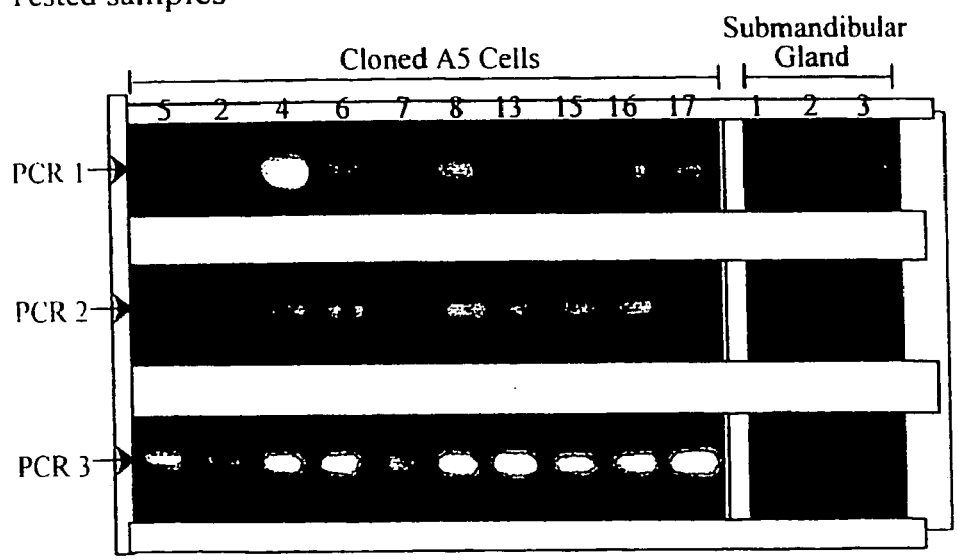

The three PCR assays shown in FIG. 6 were used to screen for possible vector integration by amplifying fragments from 5'LTR and luciferase cDNA of AdLTR-luc. The same amount of template DNA was added to all three PCR assays. The primers 5'LTRS2 (5'-TCTCCACCACCATACT-GAACC-3', SEQ ID NO: 9) and 5'LTRA1 (5'-TCAAAAC-TAGAGCCTGGACC-3', SEQ ID NO:10) produced PCR 1 (662 bp). PCR 2 (262 bp) was amplified by 5'LTRS4 (5'-TGTGGTTCTGGTAGGAGACG-3', SEQ ID NO:11) and 5'LTRA3 (5'-CCAACGTCTCTTCTTGACAT-3', SEQ ID NO:12). PCR 3 (227 bp) is a luciferase product and amplified by lucS2 (5'-AGGCGAATTATGTGTCAGAGG-3', SEQ ID NO: 13) and lucA2 (5'-TTGGGGTGTTGTAA- CAATA-3', SEQ ID NO: 14). For these three PCR assays, the negative control was genomic DNA from non-infected A5 cells. The positive control was genomic DNA from A5 cells infected 3 days before harvested DNA. If the initial PCR results showed that the PCR1 product was missing, the assays were repeated by increasing the amount of template DNA and re-amplifying at least twice. The thermal cycler used for all PCR assays was DNA Thermal Cycler 480 from PERKIN ELMER CETUS (Foster City, Calif.).

Southern Hybridization

The genomic DNA used in the Southern hybridization analyses was extracted with a Non-Organic DNA Extraction kit (Intergen). Fifteen micrograms of genomic DNA from each sample were digested with different restriction enzymes (see Results) and separated on a 1% agarose gel. Nucleic acids were then transferred to nylon membranes. The blots were separately hybridized with an $[\alpha\text{-}^{32}P]$ dCTP radiolabelled luciferase probe (probe 1; a 464 bp Eco RI/Xba I fragment from the 5'end of the luciferase cDNA), an E2B probe (probe 2; a 1.8 kb fragment from the adenoviral E2 region between Nco I sites 8,036 and 9,821 in pJM17), an E2A/E3 probe (probe 3; a 8 kb fragment from the adenoviral E2A and E3 regions between Hind III sites 22,687 and 30,697 in pJM17), and an E4 probe (probe 4; a 2.9 kb fragment from the adenoviral E4 region between Hind III sites 36,143 and 39,080 in pJM17), and autoradiographed.

FISH Detection

Cells infected with either Ad5'LTR-luc or AdCMV-luc (10 pfu/cell) were cultured for 1 week. Also, a cloned A5 cell (#13, FIG. 6), previously infected with Ad5'LTR-luc, was cultured for 7 months in vitro. FISH analyses were carried out by SeeDNA Biotech INC. (Toronto, Canada). The data reported herein represent experiments with six separate cell preparations. FISH probe 1 was a 6.4 kb fragment, which contained the 5' and 3'LTRs and the luciferase cDNA sequences. This probe was biotinylated with dATP using the BRL BioNick labeling kit. FISH probe 2 was pAC, which includes 3.1 kb of sequence from adenoviral E2B region. The third FISH probe used was an 8 kb fragment from pJM17 between Hind III sites 22,687 and 30,697 containing adenoviral E2A/E3 sequences and also used for Southern hybridizations. HSY cells infected with AdCMV-luc as a control were hybridized with pACCMV-luc as a probe. In two probe hybridization analyses, the second probe was digoxigenin labeled with dATP, also using the BRL BioNick labeling kit. As a further control for the labeling conditions in two probe analyses, the labels were reversed. The general procedure for FISH detection was performed according to published methods (Heng et al., 1992).

Example 2

Examination of Possible Retrovirus Production and Examination of Possible Contamination of Ad5'LTR-luc with the MoMLV Integrase and Reverse Transcriptase Genes To determine if infection hybrid adenovirus including a single LTR can lead to retrovirus production in vitro, a reverse transcriptase assay was carried out following infection of HSY and A5 cells with Ad5'LTR-luc (FIG. 2). If retroviruses were produced following cell line infections, the reverse transcriptase assay would be positive. As shown in FIG. 3A, no reverse transcriptase activity was found in these two cell lines after Ad5'LTR-luc infection. However, reverse transcriptase could be readily detected in positive control samples. In the same experiments, Ad5'LTR-luc infected HSY and A5 cells showed high levels of luciferase expression (FIG. 3B).

To test for any possible contamination by key MoMLV genes in our system, three PCR assays each, for MoMLV integrase and reverse transcriptase, were performed (FIG. 4A). As shown in FIGS. 4B and 4C, amplification of positive control samples readily yielded each of the three expected PCR products for both the integrase and reverse transcriptase genes. In the negative control (water) and in freshly infected A5 cells (infected with Ad5'LTR-luc three days before harvesting DNA), none of the PCR products could be amplified. Furthermore, these PCR assays were unable to detect any trace of the expected amplicons in the four A5 cell clones studied, (#s 2, 5, 7, 15; FIGS. 4D and 4E).

Example 3

Luciferase Gene Expression in Vitro and in Vivo

As representative dividing cells, the HSG, A5 and HSY cell lines, all derived from salivary epithelial cells, were used. Human mononuclear cells and macrophages, and rat hippocampus neurons were grown in primary cultures without proliferation and are generally considered to be non-dividing cells. All of these cell types were easily infected by Ad5'LTR-luc (FIGS. 5A, 5B). Infection of these same cells with AdCMV-luc yields a similar pattern of luciferase activity, albeit approximately 10-fold higher values (see FIGS. 2A, 2B in Zheng et al., 2000). A cloned Ad5'LTR-luc infected A5 cell grown for 9 months in vitro without any special selection medium was also examined. This A5 clone (clone # 13; see FIG. 6C) exhibited comparable luciferase activity after >200 doublings over an 8-month period (FIG. 5C).

To determine if Ad5'LTR-luc can mediate long-term transgene expression in vivo, rat submandibular gland was used as a target tissue. The level of luciferase activity was initially quite high and thereafter decreased in a linear manner (FIG. 5D). After 9 weeks (last time point tested), luciferase activity was at background levels. This general pattern of luciferase activity was seen when rat submandibular glands were infected with AdCMV-luc (Zheng et al., 2000), albeit initial expression levels were higher.

Example 4

PCR Assay to Screen for Possible Vector Integration

PCR provides a simple and fast method to screen for possible hybrid adenoretroviral vector integration in infected cells and tissues (Zheng et al., 2000). Thus, PCR primers were synthesized for 3 regions of Ad5'LTR-luc (FIG. 5A). The amplicon PCR 1 was upstream of the canonical break point, CATT, at the beginning of U3 in the 5'LTR of MoMLV. A second amplicon, PCR 2, was downstream of this region in the MoMLV packaging sequence, while PCR 3 was amplified from the luciferase cDNA. Therefore, if the sequence of PCR 1 is absent from a sample, it would suggest that breakage of the vector has occurred in the 5'LTR, i.e. possible integration.

FIG. 6B shows the results of positive and negative control assays for these PCR products. All three amplicons could not be amplified in the negative control (DNA from non-infected A5 cells) samples, but could be amplified in the positive control sample (DNA from A5 cells three days after infection with Ad5'LTR-luc). In the first series of experiments, A5 cells were infected with Ad5'LTR-luc and plated to form single clones, which were then grown individually. Cells clones that expressed luciferase activity were randomly selected for further study. In the ten cell clones studied (FIG. 6C), two had no detectable PCR 1 amplicon, but all clones were positive for amplicons PCR 2 and PCR 3 (FIG. 6C). While the absence of a PCR 1 product is suggestive of possible genomic integration, note that even in clones that yielded a PCR 1 amplicon, it is possible that integration occurred. This latter situation would reflect a mixture of intact (epichromosomal) and integrated vector in cells (i.e. the former would be detected even in the presence of the latter). After infection of A5 cells with AdCMV-luc amplicons PCR 1 and PCR 2 were never detected, while amplicon PCR 3 was consistently detected (FIG. 3B).

For in vivo samples, the PCR 1 product could not be amplified from 2 submandibular glands (FIG. 6C). The PCR 3 product was found in all submandibular gland samples, although no luciferase activity could be measured (FIG. 5D; 9 week time point); this was likely due to the greater sensitivity of the PCR assay.

Example 5

Determination of Vector Integration by Southern Hybridization

Southern hybridization was carried out on DNA samples obtained from four A5 cell clones, # 2, 5, 7 and 15 (which were infected with AdLTR-luc; FIG. 6), with four probes. Probe 1 was a luciferase fragment obtained from the 5'end of the luciferase cDNA. Probes 2–4 were used to test if adenoviral sequences located downstream of the luciferase cDNA were involved in the integration event. Probe 2 was derived from the adenoviral E2B region. Probe 3 represents adenoviral E2A/E3 region sequences. Probe 4 represents adenoviral E4 region sequences.

First, it was important to know if the luciferase cDNA remained intact in these clones. Bam HI/Nco I digestion of Ad5'LTR-luc results in a 3 kb band that includes the entire luciferase cDNA plus 336 bp of adenoviral E2B sequence (FIG. 7A; see enzyme target sites). As shown in FIG. 7B, use of probe 1 indicates that all cloned cells had the same ~3 kb band present as the positive control sample. Therefore, all four cloned cells contained an intact luciferase cDNA. All of these cloned cells also exhibited considerable luciferase activity.

It was then determined whether vector sequences were integrated. Thus, each set of samples was digested with specific restriction endonucleases, electrophoresed and transferred to nylon membranes. Each Southern blot, representing a different enzyme digestion scheme, was hybridized four times (sequentially after stripping) with probes 1, 2, 3 or 4. For these experiments, the genomic DNA samples were digested by either Bam HI/Nco I (FIG. 7), Spe I (FIG. 8), Bam HI alone (FIG. 9), Xho I (FIG. 11) or Kpn I (FIG. 12).

Each figure (FIGS. 7–12, panel A) shows the enzyme target site locations in Ad5'LTR-luc, along with the sequence position of probes 1, 2, 3 and 4. In these experiments, if cloned cell samples had the same band size as seen with the positive control samples, it suggested that this part of Ad5'LTR-luc was not broken and was not integrated into the genome. Conversely, if there was a hybridized band of different size, it meant that integration had occurred.

In FIG. 7, panel B, probes 1, 2 and 3 panel all show hybridization positive bands of essentially the same size and pattern as the positive control. Therefore, this result indicated that there was no break in the probe 1, 2 or 3 regions. However, results obtained with probe 4 were different from the control, and showed the absence of the second hybridization band (representing a sequence from 37,986 bp to the end of virus) in all cloned cells, suggesting the possibility of a breakpoint in the E4 sequence.

Next, samples digested with Spe I were analyzed (FIG. 8). There are three Spe I sites in Ad5'LTR-luc; two in the 5'LTR (909 and 1966 bp) and one just downstream of the probe 3 site at 31,477 bp (FIG. 8A). Probes 1 and 2 gave similar hybridization results with the cloned cell samples. In clones 2 and 7, a second hybrid band smaller in size than the positive control was seen indicating a possible second integration site (FIG. 8B). With probe 3, all lanes showed a similar band to the uppermost band of the corresponding samples in the probe 1 and 2 panels, and in addition the clone 15 sample showed a distinct small band present. All Spe I digested cloned cell samples showed different hybridization band sizes with probe 4 than seen with the positive control. Thus, there was (i) possibly a break in the 5'LTR between the second of the LTR's Spe I sites and the luciferase cDNA, (ii) likely no break in the sequence from the luciferase cDNA though the third Spe I site downstream of probe 3. In addition, there was (iii) support for the existence of a break in the E4 region.

As shown in FIG. 9, the results of Southern analyses with samples digested with Bam HI alone yield quite similar results. There are 3 Bam HI sites in Ad5'LTR-luc (FIGS. 7, 9); at the 5' and 3'ends of the 5'LTR, and at the 3'end of the E2 region (mid-portion of probe 3). These are similar in distribution to Spe I sites. A5 cells were also infected by AdCMV-luc and selected. After growth of these cells in vitro for ~1 month, DNA was prepared. Following digestion with Bam HI, Southern hybridization was also performed. With all these luciferase expressing A5 cell isolates, all four probes hybridized to bands identical to that seen with the positive control samples (FIG. 10), indicating no integration occurred.

DNA samples digested with Xho I were then examined (FIG. 11). There are five Xho I target sites in Ad5'LTR-luc (FIG. 11A). In general, hybridization of Xho I digested samples with probes 1, 2 and 4 showed a different pattern and size of bands than seen with the positive control. Note that the same hybridization pattern was seen with probes 1 and 2, indicating a break upstream of the probe 1 hybridization site. When DNA samples obtained from AdCMV-luc infected A5 cells are digested with Xho I and hybridized to a luciferase probe, no evidence for vector integration is seen (Zheng et al., 2000; FIG. 4). Conversely, all experimental samples gave results with probe 3 hybridization that were generally comparable to the positive control. These results were consistent with the previously described findings (FIGS. 7–9), i.e. these Southern analyses indicate that the entire E2 and E3 adenoviral sequence was integrated into genomic DNA of the cloned A5 cells, along with part of the 5'LTR and the luciferase cDNA.

DNA samples digested with Kpn I (FIG. 12), digestion were also examined to determine if there was breakpoint in E4 region. Probes 1–3 resulted in a similar pattern of hybridization positive bands for the positive control samples, and all four cloned cell samples (FIG. 12B). Conversely, results obtained with probe 4 with cloned cell samples were all different from the control, i.e. the absence of the second hybridization band (from 37,853 bp to the end of virus). This is also consistent with a possible breakpoint in the E4 sequence was between 37,986 bp and the end of virus, as suggested by the results shown in FIG. 7B using probe 4.

DNA samples from amplified individual A5 cells (for 30 days) (#s 1, 2 and 3) infected with AdCMV-luc (same as FIG. 10) were examined after digestion with Nco I (FIG. 13). The positive control sample was from infected A5 cells with AdCMV-luc 3 days before harvesting DNA. Genomic DNAs digested with Nco I show a similar pattern in all three samples compared to the positive control. This indicates that no integration occurred in these AdCMV-luc infected cells.

In order to help to localize the break point in the 5'LTR more definitively, three additional restriction endonucleases, Nco I, Not I and Kpn I, were used to individually digest DNA samples. The MoMLV 5'LTR fragment has target sides for all these three enzymes; Nco I (at 647 bp), Not I (at the beginning of 5'LTR) and Kpn I (at 260 bp, 443 bp and 1720 bp). The next target sites for each of these three enzymes downstream of the 5'LTR are all located in the E2B region, i.e., a region in which there appeared to be no break from the above, earlier Southern analyses. Thus, if there was a break downstream of the target sites for these enzymes in the 5'LTR, the resulting Southern blots would show different band sizes from the positive control. In FIG. 14, all samples were hybridized to probe 1 and generally showed different sized bands compared with the positive control; with Nco I and Kpn I these were slightly smaller, and with Not I the bands were larger. Therefore, these results indicate that the 5'LTR break points were located downstream of the Nco I, Not I and Kpn I target sites, likely between the Spe I site at 1966 bp and 3'end of the 5'LTR.

Figure 5:
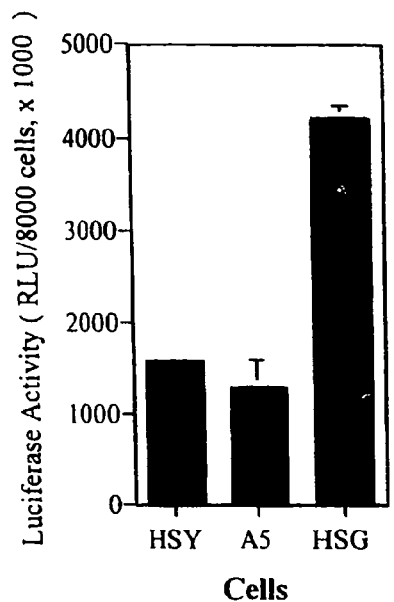
FIG. 5 is a series of graphs demonstrating luciferase expression in vitro and in vivo when different cell types were infected with Ad5'LTR-luc. Cells were infected with Ad5'LTR-luc at 50 pfu/cell.
Figure 5:
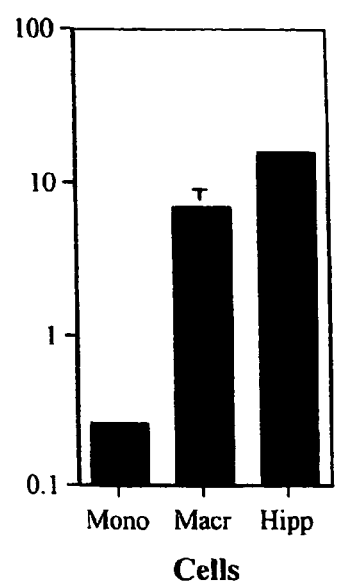
Figure 5:
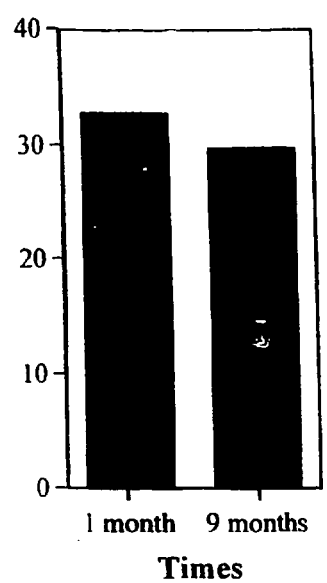
Figure 5:
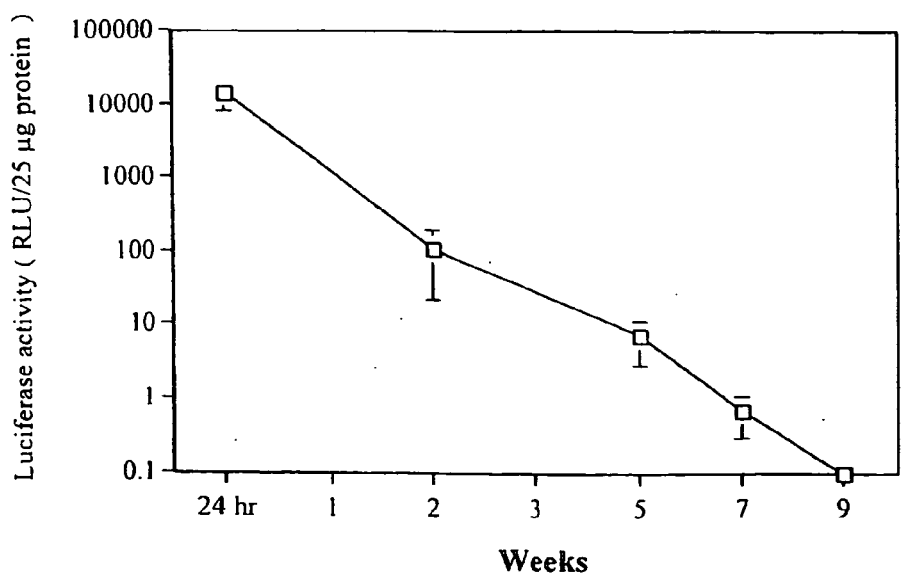

The last set of Southern hybridization analyses performed examined the genomic DNA of an A5 cell clone (#13; FIG. 5) from 1 and 7 months post-infection with Ad5'LTR-luc. These DNA samples were digested with either Bam HI/Nco I, Not I or Bam HI alone. Hybridization was carried out on the same blot by sequential hybridization (after stripping) with probes 1, 2 and 3. As shown in FIG. 15, there is little to no change in the cloned cell DNA band pattern after passaging over this time interval. This is consistent with the notion that the Ad5'LTR-luc vector mediated stable genomic integration into these cells.

Example 6

Use of FISH to Examine Vector Integration

Fluorescence in situ hybridization (FISH) was used to directly visualize the integration of Ad5'LTR-luc in A5 (FIGS. 16A–D) and HSY (FIGS. 16E and F) cells. Results in FIG. 16 show that positive FISH results were obtained with all three probes used, luciferase cDNA plus LTR (probe 1), E2B (probe 2), and E2A/E3 (probe 3). This suggests all three vector regions are integrated. Eight to 12% of mitotic cells were positive for integration after hybridization with the luciferase probe (FIG. 16A). Twenty-six percent of mitotic cells were positive for integration after hybridization with the E2B probe (FIG. 16B). Six to 8% of mitotic cells were positive for co-integration when cell chromosomes were hybridized with both the luciferase and E2A/E3 probes (FIG. 16C). This latter result indicates that over 20 kb of Ad5'LTR-luc were integrated into the A5 cell genome. The integration events appeared to be random and occasionally more than one integration event was seen in one mitotic nucleus (e.g., FIG. 16A). In FIG. 16D results are shown from an A5 cell clone #13 (which is the same clone as tested in experiments shown in FIG. 14), infected with Ad5'LTR-luc and cultured for 7 months. About 80% of the mitotic cells from this clone were positive for integration by probe 1. Also, the integration site for clone # 13 was identical in all mitotic cells examined, at either rat chromosome 7 or 8 (we could not distinguish these). When HSY cells were infected with Ad5'LTR-luc, 33% of mitotic cells examined were positive for integration after hybridization with probe 1 (FIG. 16E). No integration, however, was detected in HSY cells after infection with AdCMV-luc (FIG. 16F).

The series of experiments described here was begun to help understand the mechanism by which the recently reported hybrid adenoretroviral vector, AdLTR-luc achieved genomic integration (Zheng et al., 2000). AdLTR-luc incorporates both the 5' and 3'LTRs of MoMLV flanking the luciferase cDNA. The vector Ad5'LTR-luc was originally constructed as a control, as it was believed that expected this vector would not integrate as it only contained a single retroviral LTR. Unexpectedly, Ad5'LTR-luc was able to integrate in a most unusual manner, including at least ~20 kb of foreign DNA sequence. Ad5'LTR-luc could efficiently infect dividing and non-dividing cells in vitro, as well as rat submandibular gland in vivo.

However, Ad5'LTR-luc did not lead to long-term transgene expression in vivo. The latter result likely occurred because a substantial amount of adenoviral sequence, notably the E2 and E3 regions, was integrated into the genome along with the part of 5'LTR and the luciferase reporter gene. These sequences would be able to continue to express adenoviral proteins, rendering the transduced cells immunological targets. Removal of the E2 and E3 regions is likely to result in long-term transgene expression.

Several different types of experiments support a conclusion that the 5'LTR sequence from MoMLV used here was sufficient to mediate Ad5'LTR-luc integration. These include PCR assays, Southern hybridization analyses (using 7 different restriction endonuclease digestions), and FISH analyses (6 assays with multiple probes). The FISH analyses performed suggest that integration of a hybrid adenoviral vector including a single retroviral LTR was a reasonably common event (6–33% of mitotic nuclei in uncloned cells). Our experiments (Zheng et al., 2000) with AdLTR-luc provided no evidence for inclusion of adenoviral sequences in the integrated fragment. A conventional adenovirus, AdCMV-luc, analogous to Ad5'LTR-luc but containing the CMV promoter/enhancer instead of the 5'LTR, also showed no evidence for any integration by PCR, Southern hybridization and FISH analyses (see above and Zheng et al., 2000).

All of these studies are also consistent with the 5'LTR sequence used here being involved in mediating a highly atypical integration of both the encoded transgene and a relatively large piece of adenoviral DNA. Using Southern analyses with cloned A5 cells, the breakpoint regions in Ad5'LTR-luc were defined. One break occurred in the 5'LTR between nt 1966–2700. The second break, occurred in the E4 adenoviral sequence, between nt 37,986 and the end of the virus. Additionally, the results shown in FIGS. 8 and 9 support a possibility for a second integration event in clones #2 and 7. The FISH results shown in FIG. 16A are also consistent with this possibility. Without being bound by theory, the 5'LTR may not be alone in directing integration. Interactions between the 5'LTR and certain cis-acting adenoviral elements may also be involved in this process. Construction of a hybrid adenoviral vector including a single retroviral LTR as an E2/E3/E4 deleted, "gutted", vector, may allow the use of the LTR to integrate a rather large-sized therapeutic gene into the genome.

The results demonstrated herein are not necessarily consistent with the classic rules of retroviral biology. Classically, for retroviral integration into the host cell genome to occur, two cis elements (5' and 3'LTR sequences) are required, along with virally encoded integrase (Asante-Appiah and Skalka, 1997; Brown, 1997; Donehower and Varmus, 1984; Goff, 1992; Panganiban and Temin, 1983; 1984; Roth et al., 1989; Schwartzberg et al, 1984). In the experiments presented herein, no evidence of retroviral contamination of, or generation in, the target cell lines used was found (i.e. negative results for reverse transcriptase analyses, and PCR assays for MoMLV integrase and reverse transcriptase). In addition, it was observed that one cell clone, infected by Ad5'LTR-luc, cultured without any selection medium for >9 months, continued to exhibit stable genomic integration. Thus, these data provide evidence for a novel function for the MoMLV 5'LTR sequences employed.

Transgenes delivered by a retroviral or adeno-associated viral (AAV) vector can integrate into the genome and lead to stable expression (Carter and Samulski, 2000; Tal, 2000; Takeuchi and Pizzato, 2000; Wang et al., 2000). However, with both conventional retroviral and AAV vectors there are size limitations for the transgene. Adenoviral vectors are quite large, about 36 kb. Thus, there theoretically is a large insert capacity in adenoviral vectors. Recently, several laboratories have developed helper-dependent (or "gutted") adenoviral vectors, which are deleted in all adenoviral protein-coding sequences (e.g., Maione et al., 2000; Morral et al., 1999; Morsy et al., 1998; Morsy and Caskey, 1999). Results from in vivo studies employing these "gutted" vectors have shown that such a construct significantly reduces vector immunogenicity and prolongs transgene expression, in addition to enhancing the safety profile of the vector and increasing insert capacity. For some conditions targeted by gene therapy, e.g. Duchenne's muscular dystrophy, the native gene is quite large. Additionally, physiological regulation of a relatively small gene may need significantly sized cis regulatory elements. The results presented herein demonstrate that use of the a single LTR (e.g. the 5'MoMLV LTR) can facilitate these goals, in conjunction with using helper-dependent adenoviral vector technology.

Example 7

Construction of a Gutted Hybrid Adenoviral Vector Including a Single Retroviral LTR First generation adenoviral vectors, with E1 or E1 and E3 deleted, efficiently and widely infect dividing cells and non-dividing cells in vitro and in vivo. However, these vectors do not overcome the host's response to adenoviral proteins. In addition, in some cell types, there are problems with first generation associated with transgene transfection and cytotoxicity using the first generation vectors. To overcome these problems a "gutted" adenoviral vector is produced, in which the coding sequences (e.g. E1, E2, E3 and E4) are deleted (Hammerschmidt D E, *J. Lab. Clin. Med.,* 134(3):C3, 1999; Parks et al., *Gene Ther.,* 6(9):1565–73, 1999, both incorporated herein by reference). This host immune response is decreased when the gutted vector is used in vivo. The cytotoxicity associated with first generation vectors is also decreased when the gutted vector is used.

Restriction enzymes are used to cleave 5'LTR from pXT1 plasmid to insert into a gutted adenoviral vector. In one embodiment, a transgene is included in the gutted vector. In another embodiment, one, two or three nucleic acid sequences encoding marker peptides (e.g. luciferase, green fluorescent protein, red fluorescent protein) each operably linked to the same or to different promoters (viral promoters, CMV, RSV, SV40 or tissue specific promoters such as amylase or kallikrein promoters) are inserted downstream of 5'LTR. These constructs are then tested in vitro and in vivo for integration into the host genome and long-term gene expression. The immune response of the host and cytotoxicity are also assessed. Deletion of E1, E2, E3 and E4 results in decreased host immune response (e.g. a T cell or a B cell response). In addition, deletion of E1, E2, E3 and E4 results in long-term expression of the transgene.

The methods described herein demonstrate that a hybrid vector including only one LTR can integrate into the genome and thus allow a transgene to stably persist in cells. As described herein, the inclusion of one LTR in an adenoviral vector allows for the insertion of a large transgene (e.g. up to 20 kb of nucleic acid) to integrate into the genome. The vectors disclosed herein can be used to need to deliver more than one coding sequence, and to regulate therapeutic gene expression and function.

Example 8

Testing Hybrid Adenoviral Vectors in Disease Models in Vivo

The hybrid adenoviral vectors described in the above examples can be tested for their ability to express a transgene in mouse models which have been generated for various diseases. Mice which are functionally deleted for a gene, are infected with a hybrid adenoviral vector containing a transgene designed to complement the gene deficiency. Mice are then screened for their ability to express the transgene, and the ability of the transgene to correct the phenotypic affect of the gene deletion.

A hybrid adenoviral vector can be introduced into any organism whose genome has been altered by in vitro manipulation of the early embryo or fertilized egg or by any transgenic technology to induce a specific gene knockout. A gene knock-out is the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. A hybrid adenoviral vector including a single LTR can be introduced, using any method known to one of skill in the art, to introduce a nucleic acid sequence into an animal produced by any transgenic technology.

In another embodiment, the hybrid adenoviral vectors can be used to transform mouse embryos. Transgenic animals can be produced by introducing into embryos (e.g. a single celled embryo) a hybrid adenoviral vector including a single LTR, in a manner such that the polynucleotides are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, viral infection or other means, the transformed cells are then introduced into the embryo, and the embryo then develops into a transgenic animal. In a preferred method, developing embryos are infected with a hybrid adenovirus containing the desired DNA, and transgenic animals produced from the infected embryo.

In one method DNA is injected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature*, 315:680, 1985; Purcel et al., *Science*, 244:1281, 1986; Wagner et al., U.S. Pat. No. 5,175,385; Krimpenfort et al., U.S. Pat. No. 5,175,384, the respective contents of which are incorporated by reference.

The nucleotide sequence of interest can be fused in proper reading frame under the transcriptional and translational control of a promoter to produce a genetic construct. The genetic construct is then amplified, for example, by preparation in a bacterial vector, according to conventional methods. See, for example, the standard work: Sambrook et al., *Molecular Cloning: a Laboratory Manual*, Cold Spring Harbor Press, 1989, the contents of which are incorporated by reference. The amplified construct is thereafter purified for use in producing transgenic animals.

Example 9

Antisense

In one embodiment, a hybrid adenoviral vector includes an antisense molecule as the transgene. In general, the antisense molecule must by able to bind complementarily to the target RNA. Complementary binding occurs when the base of one molecule forms a hydrogen bond with another molecule. Normally the base Adenine (A) is complementary to thymidine (T) and uracil (U), while cytosine (C) is complementary to guanine (G). Therefore, the sequence 5'-TCGT-3' of the antisense molecule will bind to ACUC of the target RNA, or 5'-ACTC-3' of the target DNA. Additionally, in order to be effective, the antisense and sense molecules do not have to be 100% complementary to the target RNA or DNA.

The antisense polynucleotides can vary in length. Generally, a longer complementary region will give rise to a molecule with higher specificity. When the hybrid adenoviral vector is introduced into a host cell, the host cell supplies the necessary components for transcription of the therapeutic antisense molecule.

Catalytic nucleic acid and other oligomeric molecules can be designed which degrade target sequences and included in a hybrid adenoviral vector of the invention. Such catalytic antisense molecules can contain complementary regions that specifically hybridize to the target sequence, and non-complementary regions which typically contain a sequence that gives the molecule its catalytic activity.

A particular type of catalytic nucleic acid antisense molecule is a ribozyme or anti-sense conjugates, which may be used to inhibit gene expression (e.g. see PCT publication WO 9523225, and Beigelman et al. *Nucl. Acids Res.* 23:4434–4442, 1995). Examples of oligonucleotides with catalytic activity are described in WO 9506764, WO 9011364, and Sarver et al., *Science* 247:1222–1225, 1990.

The relative ability of an oligomer such as a polynucleotide to bind to a complementary strand is compared by determining the melting temperature of a hybridization complex of a polypeptide and its complementary strand. The melting temperature ($T_m$), a characteristic physical property of double helices, denotes the temperature in degrees Centigrade at which 50% helical versus coiled (unhybridized) forms are present. Base stacking, which occurs during hybridization, is accompanied by a reduction in UV absorption (hypochromicity). A reduction in UV absorption indicates a higher $T_m$. The higher the $T_m$ the greater the strength of the binding of the hybridized strands. As close to optimal fidelity of base pairing as possible achieves optimal hybridization of a polynucleotide to its target RNA.

Example 10

Gene Therapy Using Hybrid Adenoviral Vectors

The present invention provides the transformation of cells in vitro and in vivo. The nucleic acids can transfected into cells by packaging the hybrid adenoviral vector in an adenoviral particle. Thus, both dividing and non-dividing cells can be transformed.

In one particular class of embodiments, adenoviral vectors are used in cell transformation procedures for gene therapy. Gene therapy provides methods for combating chronic infectious diseases such as HIV, as well as non-infectious diseases such as cancer and birth defects such as enzyme deficiencies.

A new gene therapy approach for patients using the hybrid adenoviral vectors taught by the present invention, is now made possible. Essentially, cells can be removed from a subject having deletions or mutations of a gene, and then the hybrid adenoviral vectors (which contains the therapeutic transgene) is introduced into the cell. These transfected cells will thereby produce functional transgene protein and can be reintroduced into the patient. Methods described in U.S. Pat. No. 5,162,215 (Bosselman et al.) demonstrate how to detect the presence and expression of a gene of interest in target cells. Methods described in U.S. Pat. No. 5,741,486 (Pathak et al.) teach the use of viral vectors in gene therapy. Such methods can be applied to the hybrid adenoviral vectors of the present invention, for example in gene therapy.

In addition, the hybrid adenoviral vectors can be introduced into a subject in vivo. The scientific and medical procedures required for human cell transfection are now routine procedures. The provision herein of hybrid adenoviral vectors now allows the development of human and non-human gene therapy based upon these procedures.

In some embodiments, the present invention relates to a method of treating patients which underexpress a gene, or in which greater expression of the gene is desired. These methods can be accomplished by introducing a transgene coding for the underexpressed gene into a hybrid adenoviral vector, which is subsequently introduced into the patient.

In some of the foregoing examples, it may only be necessary to introduce the genetic or protein elements into only certain cells or tissues. However, in some instances (i.e. tumors), it may be more therapeutically effective and simple to treat all of the patients cells, or more broadly disseminate the vector, for example by intravascular administration.

The hybrid adenoviral vectors can be administered to the patient by any method which allows the vectors to reach the appropriate cells. These methods include injection, infusion, deposition, implantation, or topical administration. Injections can be intradermal or subcutaneous.

In addition, the hybrid adenoviral vector can be designed to use different promoters to express the transgene. In one embodiment, the retroviral LTR sequence can serve as a promoter for expression of the transgene. Thus, in one example, a therapeutic nucleic acid is placed under the control of the retroviral LTR promoter. In another embodiment, the transgene is operatively linked to a heterologous promoter (e.g. the CMV promoter). In yet another embodiment, the transgene is operatively linked to a tissue specific promoter (e.g. the immunoglobulin promoter), such that the expression of the transgene occurs only in a tissue of interest.

Ex Vivo Transformation of Cells

Ex vivo methods for introducing a hybrid adenoviral vector in a cell in an organism involve transducing the cell ex vivo, and then introducing the cell into the organism. For example, adenoviral particles including adenoviral capsid proteins and a hybrid adenoviral vector of the invention can be used to treat autologous cells isolated from a subject. In one embodiment, the cells are lymphocytes, macrophages or stem cells isolated or cultured from a subject. Alternatively, the cells can be heterologous cells such as those stored in a cell bank (e.g., a blood bank).

In one specific non-limiting example, the cells are T cells. Several techniques are known for isolating T cells. In one method, Ficoll-Hypaque density gradient centrifugation is used to separate PBMC from red blood cells and neutrophils according to established procedures. Cells are washed with modified AIM-V [which consists of AIM-V (GIBCO) with 2 mM glutamine, 10 µg/ml gentamicin sulfate, 50 µg/ml streptomycin) supplemented with 1% fetal bovine serum (FBS)]. Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.). Transduced cells are prepared for reinfusion according to established methods. See Abrahamsen et al., *J. Clin. Apheresis* 6:48–53, 1991; Carter et al. *J. Clin. Arpheresis* 4:113–117, 1988; Aebersold et al., *J. Immunol. Methods* 112: 1–7, 1988; Muul et al., *J. Immunol. Methods* 101: 171–181, 1987; and Carter et al., *Transfusion* 27:362–365, 1987).

In another embodiment, adenoviral particles including adenoviral capsid proteins and a hybrid adenoviral vector of the invention can be used to treat a heterologous graft which is then transplanted into the subject. For example, a hybrid adenovirus of the invention can be used to infect a heart, which is subsequently transplanted into a subject requiring a heart transplant.

In Vivo Transformation of Cells

Adenoviral particles containing a hybrid adenoviral vector including a transgene encoding a therapeutic protein can be administered directly to the organism for transduction of cells in vivo. Administration is by any of the routes normally used for introducing a molecule into cells. The packaged nucleic acids are administered in any suitable manner, preferably with pharmaceutically acceptable carriers. Suitable methods of administering such packaged nucleic acids in the context of the present invention to a patient are available, and although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Injection solutions and suspensions can be prepared from sterile powders, granules, and tablets of the kind previously described. Cells transduced by the packaged nucleic acid as described above in the context of ex vivo therapy can also be administered intravenously or parenterally as described above. The dose administered to a subject, in the context of the present invention should be sufficient to effect a beneficial therapeutic response in the patient over time, or to inhibit infection by a pathogen. The dose will be determined by the efficacy of the particular transgene employed and the condition of the patient, as well as the body weight or surface area of the subject to be treated. The size of the dose also will be determined by the existence, nature, and extent of any adverse side-effects that accompany the administration of a particular vector, or transduced cell type in a particular patient.

In determining the effective amount of the hybrid adenoviral vector to be administered in the treatment of a disease, the physician or other clinician evaluates symptom or clinical parameters, including the progression of the disease. In general, the dose equivalent of a naked nucleic acid from a vector is from about 1 µg to 100 µg for a typical 70 kilogram. The exact dosage of adenoviral particles including a hybrid adenoviral vector of the invention is dependent upon a variety of factors, including the age, weight, and sex of the subject to be treated, and the nature and extent of the disease or disorder to be treated. Effective doses can be extrapolated from dose-response curves derived from in vitro or animal model test systems.

Administration can be accomplished via single or divided doses. Methods of introduction include, but are not limited to, intradermal, intramuscular, intraperitoneal, intravenous, subcutaneous, intranasal, and oral routes. Administration can be by any convenient route, for example by infusion or bolus injection, by absorption through epithelial or mucocutaneous linings (e.g., oral mucosa, rectal and intestinal mucosa, etc.). In addition, the pharmaceutical compositions can be introduced into the central nervous system by any suitable route, including intraventricular and intrathecal injection; intraventricular injection can be facilitated by an intraventricular catheter, for example, attached to a reservoir, such as an Ommaya reservoir. Administration can be systemic or local. The adenoviral particles of the invention can be administered together with other biologically active agents.

In one embodiment, it may be desirable to administer the pharmaceutical compositions of the invention locally to the area in need of treatment, for example, by local infusion during surgery, topical application, e.g., in conjunction with a wound dressing after surgery, by injection, through a catheter, by a suppository or an implant, such as a porous, non-porous, or gelatinous material, including membranes, such as silastic membranes, or fibers. In one embodiment, administration can be by direct injection at the site (or former site) of a malignant tumor or neoplastic or pre-neoplastic tissue.

The present invention also provides pharmaceutical compositions which include a therapeutically effective amount of the hybrid adenoviral vectors, alone or with a pharmaceutically acceptable carrier.

Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

The pharmaceutical compositions or methods of treatment can be administered in combination with other therapeutic treatments, such as other antineoplastic or antitumorigenic therapies.

Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the present invention are normal saline and sesame oil.

Embodiments of the invention comprising medicaments can be prepared with conventional pharmaceutically acceptable carriers, adjuvants and counterions as would be known to those of skill in the art.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. An adenovirus, comprising adenoviral capsid proteins; and an adenoviral vector comprising adenoviral ITRs flanking a packaging signal and at least a 1.0 kb of a Moloney murine leukemia virus (MoMLV) nucleotide sequence, wherein the at least 1.0 kb MoMLV nucleotide sequence comprises a single MoMLV LTR and a nucleotide sequence encoding a portion of a viral envelope protein, wherein the single MoMLV LTR is operably linked to a nucleic acid sequence of interest, wherein the adenoviral vector does not comprise a nucleic acid encoding the MoMLV gag or pol proteins, wherein the adenoviral vector does not comprise a second MoMLV LTR, and wherein the adenoviral vector is packaged in the adenoviral capsid proteins, thereby producing infective adenovirus, wherein upon infection of an isolated host cell with the adenovirus, the adenoviral vector is integrated into the genome of the isolated host cell.

2. The adenovirus of claim 1, wherein the adenoviral vector is replication-defective.

3. The adenovirus of claim 1, wherein the at least 1.0 kb nucleotide sequence of MoMLV comprises about base pair 1155 to about base pair 2168 of MoMLV.

4. The adenovirus of claim 1, wherein the single MoMLV LTR is a 5' MoMLV LTR.

5. The adenovirus of claim 1, wherein the single MoMLV LTR is a 3' MoMLV LTR.

6. The adenovirus of claim 1, wherein the nucleic acid sequence of interest encodes a polypeptide that is a marker or a therapeutic polypeptide.

7. The adenovirus of claim 1, wherein the adenoviral vector comprises a functional deletion of an essential adenoviral gene.

8. The adenovirus of claim 7, wherein the functional deletion is a mutation or a deletion of an essential gene.

9. The adenovirus of claim 8, wherein the essential adenoviral gene is E1 or E3.

10. An isolated host cell infected by the adenovirus of claim 1.

11. The adenovirus of claim 1, wherein the MoMLV LTR includes a U3, R, and a U5 element.

12. An adenoviral vector comprising two adenoviral ITRs, wherein the two adenoviral ITRs flank a packaging signal and at least a 1.0 kb of a Moloney murine leukemia virus (MoMLV) nucleotide sequence, wherein the at least 1.0 kb nucleotide sequence comprises a single MoMLV LTR and a nucleotide sequence encoding a portion of a viral envelope protein, wherein the single retroviral LTR is operably linked to a nucleic acid sequence of interest, wherein the adenoviral vector does not comprise a nucleic acid sequence encoding the MoMLV gag or pol proteins, wherein the adenoviral vector does not comprise a second MoMLV LTR, and wherein upon introduction into an isolated host cell, the adenoviral vector integrates into the genome of the isolated host cell.

13. The adenoviral vector of claim 12, further comprising a nucleic acid sequence encoding an adenovirus capsid protein.

14. The adenoviral vector of claim 12, wherein the adenoviral vector is a replication deficient adenoviral vector.

15. An isolated host cell transformed with the vector of claim 13.

16. A composition, comprising:
   (a) an adenoviral vector comprising a 5' adenoviral ITR, a transgene, and a 3' adenoviral ITR, wherein the adenoviral vector further comprises at least a 1.0 kb of a Moloney murine leukemia virus (MoMLV) nucleotide sequence, wherein the at least 1.0 kb MoMLV nucleotide sequence comprises a single MoMLV LTR and a nucleotide sequence encoding a portion of a viral envelope protein, wherein the adenoviral vector does not comprise a second MoMLV LTR, wherein the adenoviral vector is replication defective, and wherein upon introduction into an isolated host cell, the adenoviral vector integrates into the genome of the isolated host cell; and
   (b) a pharmaceutically acceptable carrier.

17. The adenovirus of claim 1, wherein the nucleic acid sequence of interest encodes a marker.

18. The adenovirus of claim 17, wherein the marker is green fluorescent protein or luciferase.

19. The adenovirus of claim 1, further comprising a heterologous promoter operably linked to the nucleic acid of interest.

20. The adenovirus of claim 19, wherein the promoter is a cytomegalovirus (CMV) promoter.

21. The adenoviral vector of claim 12, further comprising a heterologous promoter operably linked to the nucleic acid of interest.

22. The adenoviral vector of claim 21, wherein the promoter is a cytomegalovirus (CMV) promoter.

23. The composition of claim 16, wherein the adenoviral vector comprises a heterologous promoter operably linked to the transgene.

24. The isolated host cell of claim 10, wherein the cell is a human cell.

25. The adenovirus of claim 1, wherein the adenoviral vector comprises about 2.7 kb of a MoMLV nucleotide sequence comprising the single MoMLV LTR.

26. The adenoviral vector of claim 12, comprising about base pair 1155 to about base pair 2168 of the MoMLV nucleotide sequence.

27. The adenoviral vector of claim 12, comprising about 2.7 kb of a MoMLV nucleotide sequence comprising the single MoMLV LTR.

28. The composition of claim 16, wherein the adenoviral vector comprises about base pair 1155 to about base pair 2168 of the MoMLV nucleotide sequence.

29. The composition of claim 16, wherein the adenoviral vector comprises about 2.7 kb of the MoMLV nucleotide sequence comprising the single MoMLV LTR.

* * * * *

SEQUENCE LISTING

```
<160> NUMBER OF SEQ ID NOS: 14

<210> SEQ ID NO 1
<211> LENGTH: 54
<212> TYPE: DNA
<213> ORGANISM: Artificial Sequence
<220> FEATURE:
<223> OTHER INFORMATION: Oligonucleotide primer

<400> SEQUENCE: 1
ggggggatcc aatcatcacc ctagacttgt gcacaagctt tgcaggtctc agtg        54

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 2
caagtcaacg ccagcaagtc tg                                           22

<210> SEQ ID NO 3
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 3
gacttgtgca caagctttgc aggtctcagt g                                 31

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
catgtcaggg tcagggaagt ttac                                         24

<210> SEQ ID NO 5
```

```
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 5
tggagagatc cagagatggg aatc                                           24

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 6
caccctgttt gatgaggcac tg                                             22

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 7
gggcagttag aagagcttgc ttg                                            23

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 8
ccaaggtccc agtttttgcg                                                20

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 9
tctccaccac catactgaac c                                              21

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
tcaaaactag agcctggacc                                                20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
```

```
tgtggttctg gtaggagacg                                               20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 12
ccaacgtctc ttcttgacat                                               20

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 13
aggcgaatta tgtgtcagag g                                             21

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 14
ttggggtgtt gtaacaata                                                19
```